United States Patent
Shundo et al.

(10) Patent No.: US 7,407,691 B2
(45) Date of Patent: *Aug. 5, 2008

(54) PHOTOPOLYMERIZABLE OXETANE DERIVATIVE AND LIQUID-CRYSTAL COMPOSITION CONTAINING IT

(75) Inventors: Ryushi Shundo, Ichihara (JP); Tomohiro Etou, Ichihara (JP); Masami Kimura, Ichihara (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 624 days.

This patent is subject to a terminal disclaimer.

(21) Appl. No.: 11/085,903

(22) Filed: Mar. 21, 2005

(65) Prior Publication Data

US 2005/0224757 A1  Oct. 13, 2005

(30) Foreign Application Priority Data

Apr. 7, 2004 (JP) ............................. 2004-112720
Dec. 7, 2004 (JP) ............................. 2004-353822

(51) Int. Cl.
*C09K 19/34* (2006.01)
*C09K 19/32* (2006.01)
*C09K 19/30* (2006.01)
*C09K 19/20* (2006.01)
*C09K 19/38* (2006.01)
*C07D 305/06* (2006.01)
*C07C 69/76* (2006.01)
*C07C 22/00* (2006.01)
*C07C 25/00* (2006.01)

(52) U.S. Cl. .............. 428/1.1; 252/299.01; 252/299.61; 252/299.62; 252/299.63; 252/299.64; 252/299.65; 252/299.66; 252/299.67; 549/510; 560/65; 570/124; 570/126; 570/129

(58) Field of Classification Search ............ 252/299.01, 252/299.61, 299.64, 299.65, 299.67, 299.62, 252/299.63, 299.66; 549/510; 560/65; 570/126, 570/129, 124; 528/417; 428/1.1

See application file for complete search history.

(56) References Cited

U.S. PATENT DOCUMENTS

| 6,666,989 | B1 | 12/2003 | Toyne et al. | ............ 252/299.01 |
| 7,070,838 | B2* | 7/2006 | Sasada et al. | ................ 428/1.1 |
| 7,101,595 | B2* | 9/2006 | Shundo et al. | ................ 428/1.1 |
| 7,157,124 | B2* | 1/2007 | Sasada et al. | ................ 428/1.1 |
| 7,300,604 | B2* | 11/2007 | Shundo | ................ 252/299.61 |
| 2005/0213009 | A1* | 9/2005 | Yanai et al. | ................ 349/137 |
| 2006/0278851 | A1* | 12/2006 | Ito et al. | ................ 252/299.64 |

FOREIGN PATENT DOCUMENTS

| JP | 2001-055573 | 2/2001 |
| JP | 2001-154019 | 6/2001 |

* cited by examiner

*Primary Examiner*—Shean C Wu
(74) *Attorney, Agent, or Firm*—J.C. Patents

(57) ABSTRACT

Provided are a liquid-crystal compound and a liquid-crystal composition containing the compound, of which the advantages are that they show nematic hybrid orientation on a rubbed TAC substrate, they are polymerizable in open air and they readily give a polymer having a high degree of polymerization even when exposed to a relatively small total quantity of light. The films formed by photopolymerizing them keep nematic hybrid orientation. The compound is represented by formula (1):

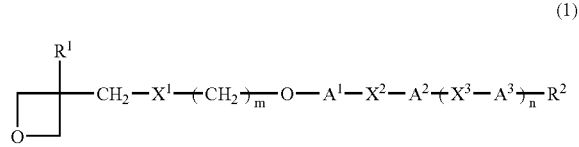

(1)

wherein $R^1$ is a hydrogen or an alkyl; $R^2$ is a hydrogen, —$OCF_3$, etc.; $A^1$ is a 1,4-phenylene, etc.; $A^2$ and $A^3$ are independently a 1,4-cyclohexylene, a 1,4-phenylene, etc.; $X^1$ is a single bond, —O—, etc.; $X^2$ and $X^3$ are independently a single bond, —COO—, —C≡C—, —CONH—, etc.; m is an integer of from 0 to 20; and n is 1 or 0.

23 Claims, No Drawings

PHOTOPOLYMERIZABLE OXETANE DERIVATIVE AND LIQUID-CRYSTAL COMPOSITION CONTAINING IT

BACKGROUND OF THE INVENTION

1. Field of the Invention

The present invention relates to a liquid-crystal compound having an oxetanyl group as a polymerizable functional group, to a composition containing the compound, to a polymer obtained by polymerizing the compound or the composition, and to their use.

The term "liquid-crystal" as referred to herein is not limited to the meaning that a compound has a liquid-crystal phase. The term may apply also to compounds not having a liquid-crystal phase by themselves but usable as a component of a liquid-crystal composition when mixed with any other liquid-crystal compound.

2. Description of the Related Art

When a polymerizable liquid-crystal compound oriented in a nematic condition is polymerized, then its orientation condition is fixed and it gives an optically-anisotropic film. The optically-anisotropic film is usable as an optically-compensatory film for liquid-crystal display devices. In particular, a shaped article fixed in hybrid-nematic orientation is usable as a viewing angle compensatory element in twisted nematic liquid-crystal display devices. When combined with a polarizer, it is also usable as an elliptically-polarizing plate.

Nematic liquid crystal orientation includes various modes of homogeneous orientation, tilt orientation, homeotropic orientation, hybrid orientation, etc. For example, disclosed is a method of adding an additive such as surfactant to a polymerizable nematic liquid-crystal material, thereby controlling it to hybrid orientation (e.g., see Patent Reference 1). However, a shaped article obtained by curing a composition that contains a non-polymerizable compound such as surfactant added thereto is problematic in that its mechanical strength and heat resistance may lower.

On the other hand, for producing an optically-compensatory film, a polymerizable liquid-crystal composition containing a suitable photopolymerization initiator added thereto is first applied onto a substrate such as rubbed triacetyl cellulose (hereinafter abbreviated to as TAC) films. Next, the liquid-crystal compound in the polymerizable liquid-crystal composition is oriented, and then polymerized through irradiation with electron rays such as UV rays to obtain an optically-anisotropic film in which the liquid crystal orientation is fixed (e.g., see Patent Reference 2).

Proposed are a branched liquid-crystal polyoxetane compound, a liquid-crystal polymer useful in liquid-crystal devices, sensors and non-linear optical devices, and an oxetane monomer for obtaining the polymer. The oxetane monomer has an improved orientation characteristic, a rapid switching speed, and a broad temperature range for liquid-crystal phase (e.g., see Patent Reference 3).

In a process of film production, the step of monomer polymerization through irradiation with UV rays requires the following three conditions from the viewpoint of the equipment and the apparatus for it.

1) Room-temperature polymerization not requiring any specific heating device.

2) Open-air polymerization not requiring purging with inert gas such as nitrogen.

3) Polymerization through irradiation with UV rays at a relatively low total quantity of light.

When a conventional acrylic polymerizable liquid-crystal material is formed into an optically-anisotropic film according to the above-mentioned process, then it brings about the following two problems.

1) In the mode of open-air UV polymerization, oxygen in air retards the polymerization, and a polymer film having good reliability such as heat resistance is difficult to obtain.

2) Since its adhesiveness to the film substrate, TAC is poor, the optically-anisotropic film obtained through polymerization peels from TAC.

A polymerizable liquid-crystal compound and a composition capable of solving these problems are desired.

Patent Reference 1: JP-A 2001-55573
Patent Reference 2: JP-A 2001-154019
Patent Reference 3: JP-T 2003-513107 (U.S. Pat. No. 6,666,989)

(The term "JP-T" as used herein means a published Japanese translation of a PCT patent application.)

An object of the invention is to provide a liquid-crystal compound that exhibits nematic hybrid orientation on a rubbed TAC substrate, and a liquid-crystal composition containing it. The film formed by photopolymerizing the compound or the composition keeps the nematic hybrid orientation. Another object of the invention is to provide a liquid-crystal compound having good polymerizability in open air and capable of readily giving a polymer that has a high degree of polymerization even at a relatively small total quantity of light applied thereto, and to provide a liquid-crystal composition that contains the compound. Still another object of the invention is to provide a shaped article having good adhesiveness to a TAC substrate.

SUMMARY OF THE INVENTION

The invention includes at least one compound of the following formula (1), a liquid-crystal composition containing the compound, and a polymer obtained by polymerizing the compound or the composition.

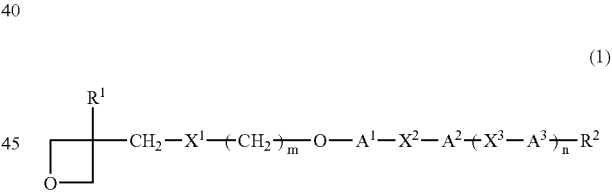

(1)

In formula (1), $R^1$ represents a hydrogen atom or an alkyl group having from 1 to 5 carbon atoms; $R^2$ represents a hydrogen atom, —NCO, —NCS, —OCHF$_2$, —CH$_2$F, —OCF$_2$CF$_2$H, —OCF$_2$CHFCF$_3$, or —Y$^1$—(CF$_2$)s—CF$_3$, in which $Y^1$ represents —O—, —S—, —COO—, —OCO—, —CO—, —CH=CH—, or —C≡C—, s indicates an integer of from 0 to 10; $A^1$ represents a 1,4-phenylene group, or a 1,4-phenylene group in which any hydrogen atom is substituted with a halogen atom, a cyano group, a methyl group, an ethyl group, a methoxy group, a hydroxy group, a formyl group, an acetoxy group, an acetyl group, a carbonylmethyl group, a carbonyltrifluoromethyl group, a difluoromethyl group, or a trifluoromethyl group; $A^2$ and $A^3$ each independently represent a 1,4-cyclohexylene group, a 1,4-phenylene group, a pyridine-2,5-diyl group, a pyridazine-3,6-diyl group, a pyrimidine-2,5-diyl group, a naphthalene-2,6-diyl group, a tetrahydronaphthalene-2,6-diyl group, a 1,4-cyclohexylene group in which any hydrogen atom is substituted with a fluorine atom, or a 1,4-phenylene group in which any hydrogen atom is substituted with a halogen atom, a cyano group, a methyl group, an ethyl group, a methoxy group, a hydroxy group, a formyl group, an acetoxy group, an acetyl group, a carbonylmethyl group, a carbonyltrifluoromethyl group, a difluoromethyl group or a trifluoromethyl group; $X^1$ represents a single bond, —O— or —OCO—; $X^2$ and $X^3$ each independently represent a single bond, —CH=CH—COO—, —OOC—CH=CH—, —OH$_2$CH$_2$—COO—, —OOC—OH$_2$CH$_2$—, —COO—, —OCO—, —OCH$_2$—, —CH$_2$—, —OCF$_2$—, —CF$_2$O—, —CH$_2$CH$_2$, —C≡C—, —NHCO—, or —CONH—; m indicates an integer of from 0 to 20; and n indicates 1 or 0.

DETAILED DESCRIPTION OF THE INVENTION

The compound and the composition containing the compound of the invention exhibits nematic hybrid orientation on a rubbed TAC substrate. The oriented film obtained by photopolymerizing the compound or the composition still keeps the nematic hybrid orientation. The compound as well as the composition containing the compound of the invention exhibits excellent polymerizability even in open air, and readily gives a polymer having a high degree of polymerization through exposure to a small total amount of light. The shaped article of the invention has good adhesiveness to a TAC substrate.

The words "liquid-crystal compound", "liquid-crystal composition" and "liquid-crystal device" may be expressed as "compound", "composition" and "device", respectively. Compounds of formula (1), formula (M1), formula (M2), formula (M3), formula (M4) and formula (M5) may be expressed as compound (1), compound (M1), compound (M2), compound (M3), compound (M4) and compound (M5), respectively.

The word "any" is meant to indicate that "not only position but also number may be any position or any number". For example, the expression saying that "any A may be substituted with B, C, D or E" is meant to include a case where one A is substituted with B, C, D or E, a case where plural A's are all substituted with any one of B, C, D and E, and in addition to these, further include a case of a combination of at least two of A substituted with B, A substituted with C, A substituted with D and A substituted with E. One example of a sentence "any —CH$_2$— may be substituted with —O—, —CH=CH— or the like" is described. When any —CH$_2$— in C$_4$H$_9$— is substituted with —O— or —CH=CH—, then a part of the resulting groups are C$_3$H$_7$O—, CH$_3$O(CH$_2$)$_2$—, CH$_3$OCH$_2$O—, H$_2$C=CH(CH$_2$)$_3$—, CH$_3$CH=CH(CH$_2$)$_2$—, and CH$_3$CH=CHCH$_2$O—. In consideration of the chemical stability of the compounds, CH$_3$OCH$_2$O— in which the two oxygen atoms are not directly adjacent to each other is preferred to CH$_3$OOCH$_2$— in which the two oxygen atoms are directly adjacent to each other.

We, the present inventors have reached an idea of combining two our findings, (1) when a polymerizable liquid-crystal compound is polymerized, then it gives an optically-anisotropic polymer, and (2) an oxetane ring-having monomer readily undergoes ring-cleavage polymerization. Based on this, we have further studied and have obtained good experimental results beyond expectations. Based on these results, we have still further studied and have completed the present invention that includes the following:

[1] A compound of a formula (1):

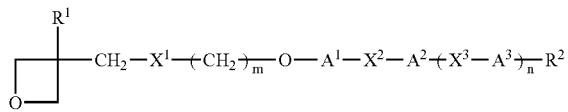

wherein $R^1$ represents a hydrogen atom or an alkyl group having from 1 to 5 carbon atoms; $R^2$ represents a hydrogen atom, —NCO, —NCS, —OCHF$_2$, —CH$_2$F, —OCF$_2$CF$_2$H, —OCF$_2$CHFCF$_3$, or —Y$^1$—(CF$_2$)s—CF$_3$, in which $Y^1$ represents —O—, —S—, —COO—, —OCO—, —CO—, —CH=CH—, or —C≡C—, s indicates an integer of from 0 to 10; $A^1$ represents a 1,4-phenylene group, or a 1,4-phenylene group in which any hydrogen atom is substituted with a halogen atom, a cyano group, a methyl group, an ethyl group, a methoxy group, a hydroxy group, a formyl group, an acetoxy group, an acetyl group, a carbonylmethyl group, a carbonyltrifluoromethyl group, a difluoromethyl group, or a trifluoromethyl group; $A^2$ and $A^3$ each independently represent a 1,4-cyclohexylene group, a 1,4-phenylene group, a pyridine-2,5-diyl group, a pyridazine-3,6-diyl group, a pyrimidine-2,5-diyl group, a naphthalene-2,6-diyl group, a tetrahydronaphthalene-2,6-diyl group, a 1,4-cyclohexylene group in which any hydrogen atom is substituted with a fluorine atom, or a 1,4-phenylene group in which any hydrogen atom is substituted with a halogen atom, a cyano group, a methyl group, an ethyl group, a methoxy group, a hydroxy group, a formyl group, an acetoxy group, an acetyl group, a carbonylmethyl group, a carbonyltrifluoromethyl group, a difluoromethyl group or a trifluoromethyl group; $X^1$ represents a single bond, —O— or —OCO—; $X^2$ and $X^3$ each independently represent a single bond, —CH=CH—COO—, —OOC—CH=CH—, —CH$_2$CH$_2$—COO—, —OOC—CH$_2$CH$_2$—, —COO—, —OCO—, —OCH$_2$—, —CH$_2$O—, —OCF$_2$—, —CF$_2$O—, —CH$_2$CH$_2$—, —C≡C—, —NHCO—, or —CONH—; m indicates an integer of from 0 to 20; and n indicates 1 or 0.

[2] The compound of [1], wherein, in formula (1), $R^1$ is a methyl or ethyl group; $R^2$ is —Y$^1$—(CF$_2$)s—CF$_3$, in which $Y^1$ is —O—, —S—, —COO—, —OCO—, —CO—, —CH=CH—, or —C≡C—, s is an integer of from 0 to 10.

[3] The compound of [1], wherein, in formula (1), $R^1$ is a methyl or ethyl group; $R^2$ is —Y$^1$—(CF$_2$)s—CF$_3$, in which $Y^1$ is —O—, s is an integer of from 0 to 10; $A^1$ is a 1,4-phenylene group, or a 1,4-phenylene group in which any hydrogen atom is substituted with a halogen atom, a methyl group, an acetyl group or a trifluoromethyl group; $A^2$ and $A^3$ are independently a 1,4-cyclohexylene group, a 1,4-phenylene group, a pyridine-2,5-diyl group, a pyridazine-3,6-diyl group, a pyrimidine-2,5-diyl group, a naphthalene-2,6-diyl group, a tetrahydronaphthalene-2,6-diyl group, or a 1,4-phenylene group in which any hydrogen atom is substituted with a halogen atom, a methyl group, an acetyl group or a trifluoromethyl group; $X^1$ is a single bond or —O—; $X^2$ and $X^3$ are independently a single bond, —CH=CH—COO—, —CH$_2$CH$_2$—COO—, —COO—, —C≡C—, or —CONH—.

[4] The compound of [1], wherein, in formula (1), $R^1$ is a methyl or ethyl group; $R^2$ is —OCF$_3$; $A^1$ is a 1,4-phenylene group, or a 1,4-phenylene group in which any hydrogen atom is substituted with a halogen atom, a methyl group, an acetyl group or a trifluoromethyl group; $A^2$ and $A^3$ are independently a 1,4-cyclohexylene group, a 1,4-phenylene group, a pyridine-2,5-diyl group, a pyridazine-3,6-diyl group, a pyrimidine-2,5-diyl group, a naphthalene-2,6-diyl group, a tetrahydronaphthalene-2,6-diyl group, or a 1,4-phenylene group in which any hydrogen atom is substituted with a halogen atom, a methyl group, an acetyl group or a trifluoromethyl group; $X^1$ is a single bond or —O—; $X^2$ and $X^3$ are independently a single bond, —CH=CH—COO—, —CH$_2$CH$_2$—COO—, —COO—, —C≡C—, or —CONH—.

[5] The compound of [1], wherein, in formula (1), $R^1$ is a methyl or ethyl group; $R^2$ is —OCF$_3$; $A^1$ is a 1,4-phenylene group; $A^2$ and $A^3$ are independently a 1,4-phenylene group or a 3-fluoro-1,4-phenylene group; $X^1$ is a single bond or —O—; $X^2$ and $X^3$ are independently a single bond, —CH=CH—COO—, —CH$_2$CH$_2$—COO—, —COO—, —C≡C—, or —CONH—; m is an integer of from 0 to 8.

[6] The compound of [1], wherein, in formula (1), $R^1$ is a methyl or ethyl group; $R^2$ is —OCF$_3$; $A^1$ is a 1,4-phenylene group; $A^2$ and $A^3$ are independently a 1,4-phenylene group or a 3-fluoro-1,4-phenylene group; $X^1$ is a single bond or —O—; $X^2$ and $X^3$ are independently a single bond, —CH=CH—COO—, —CH$_2$CH$_2$—COO—, —COO—, or —CONH—; m is an integer of from 0 to 6.

[7] The compound of [1], wherein, in formula (1), $R^1$ is a methyl or ethyl group; $R^2$ is —OCF$_3$; $A^1$ is a 1,4-phenylene group; $A^2$ and $A^3$ are independently a 1,4-phenylene group or a 3-fluoro-1,4-phenylene group; $X^1$ is a single bond or —O—; $X^2$ is —CH=CH—COO—, —CH$_2$CH$_2$—COO—, —COO—, or —CONH—; m is an integer of from 0 to 6; and n is 0.

[8] The compound of [1], wherein, in formula (1), $R^1$ is a methyl or ethyl group; $R^2$ is —OCF$_3$; $A^1$ is a 1,4-phenylene group; $A^2$ is a 1,4-phenylene group or a 3-fluoro-1,4-phenylene group; $X^1$ is a single bond or —O—; $X^2$ is —COO—; m is an integer of from 0 to 6; and n is 0.

[9] The compound of [1], wherein, in formula (1), $R^1$ is a methyl or ethyl group; $R^2$ is —OCF$_3$; $A^1$ is a 1,4-phenylene group; $A^2$ is a 1,4-phenylene group or a 3-fluoro-1,4-phenylene group; $A^3$ is a 1,4-phenylene group; $X^1$ is a single bond or —O—; $X^2$ is —CH=CH—COO—, —CH$_2$CH$_2$—COO—, —COO—, or —CONH—; $X^3$ is a single bond; m is an integer of from 0 to 6; and n is 1.

[10] The compound of [1], wherein, in formula (1), $R^1$ is a methyl or ethyl group; $R^2$ is —OCF$_3$; $A^1$, $A^2$ and $A^3$ is a 1,4-phenylene group; $X^1$ is a single bond or —O—; $X^2$ is —COO—; $X^3$ is a single bond; m is an integer of from 0 to 6; and n is 1.

[11] A liquid-crystal composition containing at least two compounds, in which at least one compound is the compound of any one of [1] to [5].

[12] The liquid-crystal composition of [11], wherein all the compounds are polymerizable compounds.

[13] The liquid-crystal composition of [11], wherein at least one compound is the compound of [1] and at least one other compound is a polymerizable compound that differs from the compound of [1].

[14] The liquid-crystal composition of [11], wherein all the compounds are the compounds of [1].

[15] The liquid-crystal composition of [11], which contains at least one compound of any one of [1] to [5] and at least one polymerizable compound selected from a group of compounds of formulae (M1), (M2), (M3), (M4) and (M5):

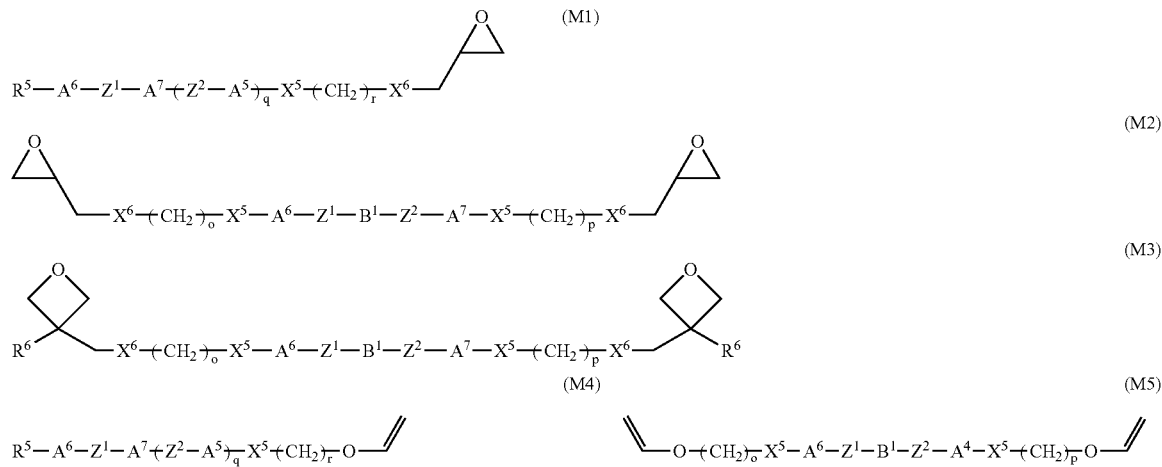

wherein $R^5$ independently represents a hydrogen atom, a fluorine atom, a chlorine atom, —CN, or an alkyl group having from 1 to 20 carbon atoms; in the alkyl group, any —CH$_2$— may be substituted with —O—, —S—, —COO—, —OCO— or —CO—, and any hydrogen may be substituted with a halogen atom; $R^6$ independently represents a hydrogen atom or an alkyl group having from 1 to 5 carbon atoms; $A^4$, $A^5$, $A^6$ and $A^7$ each independently represent a 1,4-cyclohexylene group, a 1,4-phenylene group, a pyridine-2,5-diyl group, a pyrimidine-2,5-diyl group, a naphthalene-2,6-diyl group, a fluorene-2,7-diyl group, or a 1,4-phenylene group in which any hydrogen atom is substituted with a halogen atom or a cyano group; $B^1$ independently represents a single bond, a 1,4-phenylene group, a naphthalene-2,6-diyl group, a biphenyl-4,4'-diyl group, a fluorene-2,7-diyl group, a 9-methylfluoren-2,7-diyl group, a 9-ethylfluoren-2,7-diyl group, a 9,9-dimethylfluoren-2,7-diyl group, a 9-chlorofluoren-2,7-diyl group, a 9,9-difluorofluoren-2,7-diyl group, or a 1,4-phenylene group in which any hydrogen is substituted with a halogen atom, a cyano group, a methyl group or trifluoromethyl group; $Z^1$ and $Z^2$ each independently represent a single bond, —COO—, —OCO—, —CH$_2$CH$_2$—, or —C≡C—; $X^5$ and $X^6$ each independently represent a single bond or —O—; q independently indicates 1 or 0; o, p and r each independently indicate an integer of from 0 to 20.

[16] The liquid-crystal composition of [15], which contains at least one compound of any one of [1] to [5], and at least one polymerizable compound selected from the group of compounds of formulae (M1) and (M2).

[17] The liquid-crystal composition of [15], which contains at least one compound of any one of [1] to [5], and at least one polymerizable compound selected from the group of compounds of formula (M3).

[18] The liquid-crystal composition of [15], which contains at least one compound of any one of [1] to [5], and at least one polymerizable compound selected from the group of compounds of formulae (M4) and (M5).

[19] The liquid-crystal composition of [15], which contains at least one compound of any one of [1] to [5], and at least one polymerizable compound selected from the group of compounds of formulae (M1), (M2) and (M3).

[20] A polymer obtained by polymerizing the compound of [1].

[21] A polymer obtained by polymerizing the composition of any one of [11] to [19].

[22] An optically-anisotropic shaped article comprising the polymer of [20] or [21].

[23] The optically-anisotropic shaped article of [22], wherein the liquid-crystal skeleton of the thin layer of the optically-anisotropic shaped article exhibits hybrid orientation.

[24] An optically-anisotropic shaped article comprising the polymer obtained from the liquid-crystal composition of any one of [11] to [19] that has a chiral nematic phase or a cholesteric phase, wherein the liquid-crystal skeleton of the thin layer of the shaped article exhibits a helical structure.

[25] The optically-anisotropic shaped article of [24], which selectively reflects light that falls partly or entirely within a wavelength region of from 350 to 750 nm.

[26] The optically-anisotropic shaped article of [24], which reflects light falling within a wavelength region of from 100 to 350 nm.

[27] The optically-anisotropic shaped article of any one of [24] to [26], wherein the pitch continuously varies in the direction of the thickness of the optically-anisotropic shaped article in the helical structure induced in the chiral nematic phase or the cholesteric phase.

[28] An optical device comprising the optically-anisotropic shaped article of any one of [24] to [27].

[29] A ¼ wavelength functional plate, which comprises the optically-anisotropic shaped article of any one of [24] to [27].

[30] A ½ wavelength functional plate, which comprises the optically-anisotropic shaped article of any one of [24] to [27].

[31] An optical device comprising a combination of the optically-anisotropic shaped article of any one of [22] to [27] and a polarizer.

[32] A liquid-crystal display device comprising the optically-anisotropic shaped article of any one of [22] to [27].

DESCRIPTION OF THE PREFERRED EMBODIMENTS

The compound (1) is characterized by the following:
(i) The compound (1) is a liquid-crystal compound having an oxetanyl group as a polymerizable group.
(ii) The compound (1) can undergo photopolymerization by the action of a suitable photocationic polymerization initiator.
(iii) The compound (1) is physically and chemically stable in the extreme under ordinary service condition, and is highly compatible with any other compound.

(iv) The physical properties of the compound (1) can be controlled by suitably selecting the ring, the bonding group and the side branch that constitute the compound (1), so that the compound (1) may have a high dielectric anisotropy, a low dielectric anisotropy, a high optical anisotropy, a low optical anisotropy or a low viscosity.

DESCRIPTION OF THE PREFERRED EMBODIMENTS

The oxetane derivative of the invention is described.
The oxetane derivative of the invention is represented by the following formula (1):

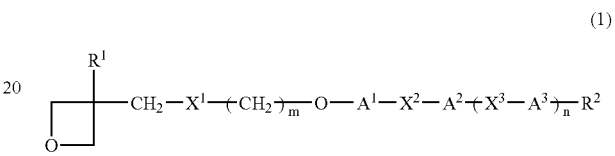

In formula (1), $R^1$ represents a hydrogen atom or an alkyl group having from 1 to 5 carbon atoms. Preferred example of $R^1$ are methyl and ethyl groups.

In formula (1), $R^2$ represents a hydrogen atom, —NCO, —NCS, —OCHF$_2$, —CH$_2$F, —OCF$_2$CF$_2$H, —OCF$_2$CHFCF$_3$—, or —Y$^1$—(CF$_2$)s—CF$_3$, in which Y$^1$ represents —O—, —S—, —COO—, —OCO—, —CO—, —CH=CH—, or —C≡C—, s indicates an integer of from 0 to 10.

$R^2$ is preferably a polar group of —Y$^1$—(CF$_2$)s—CF$_3$, in which Y$^1$ is —O—, —S—, —COO—, —OCO—, —CO—, —CH=CH—, or —C≡C—, and s is an integer of from 0 to 10.

More preferably, $R^2$ is —Y$^1$—(CF$_2$)s—CF$_3$, in which Y$^1$ is —O—, and s is an integer of from 0 to 10. Even more preferably, $R^2$ is —Y$^1$—(CF$_2$)s—CF$_3$, in which Y$^1$ is —O—, and s is 0; concretely, it is —OCF$_3$. The polymerizable liquid-crystal composition comprising such a polar compound readily undergoes hybrid orientation on a rubbed TAC substrate.

In formula (1), $A^1$ is a cyclic-structured divalent group, representing a 1,4-phenylene group, or a 1,4-phenylene group in which any hydrogen atom is substituted with a halogen atom, a cyano group, a methyl group, an ethyl group, a methoxy group, a hydroxy group, a formyl group, an acetoxy group, an acetyl group, a carbonylmethyl group, a carbonyltrifluoromethyl group, a difluoromethyl group or a trifluoromethyl group. Preferably, $A^1$ is a 1,4-phenylene group, or a 1,4-phenylene group in which any hydrogen atom is substituted with a halogen atom, a methyl group, an acetyl group or a trifluoromethyl group. Preferred examples of $A^1$ are mentioned below.

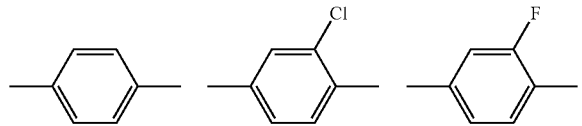

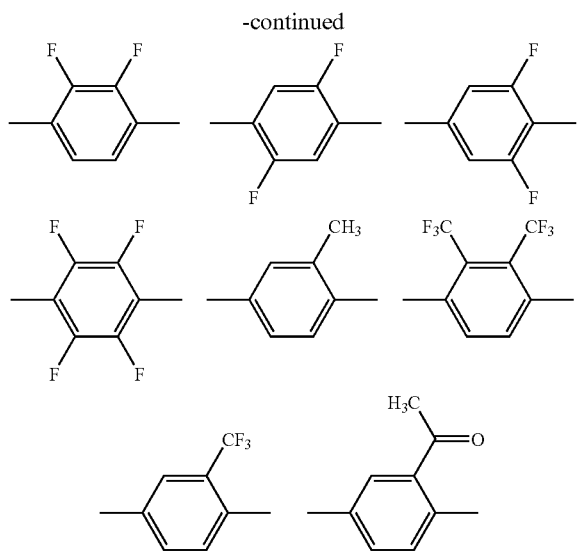

In formula (1), A² and A³ each are a cyclic-structured divalent group, independently representing a 1,4-cyclohexylene group, a 1,4-phenylene group, a pyridine-2,5-diyl group, a pyridazine-3,6-diyl group, a pyrimidine-2,5-diyl group, a naphthalene-2,6-diyl group, a tetrahydronaphthalene-2,6-diyl group, a 1,4-cyclohexylene group in which any hydrogen atom is substituted with a fluorine atom, or a 1,4-phenylene group in which any hydrogen atom is substituted with a halogen atom, a cyano group, a methyl group, an ethyl group, a methoxy group, a hydroxy group, a formyl group, an acetoxy group, an acetyl group, a carbonylmethyl group, a carbonyltrifluoromethyl group, a difluoromethyl group or a trifluoromethyl group. Preferably, A² and A³ are independently a 1,4-cyclohexylene group, a 1,4-phenylene group, a pyridine-2,5-diyl group, a pyridazine-3,6-diyl group, a pyrimidine-2,5-diyl group, a naphthalene-2,6-diyl group, a tetrahydronaphthalene-2,6-diyl group, or a 1,4-phenylene group in which any hydrogen atom is substituted with a halogen atom, a methyl group, an acetyl group or a trifluoromethyl group. Preferred examples of A² and A³ are mentioned below.

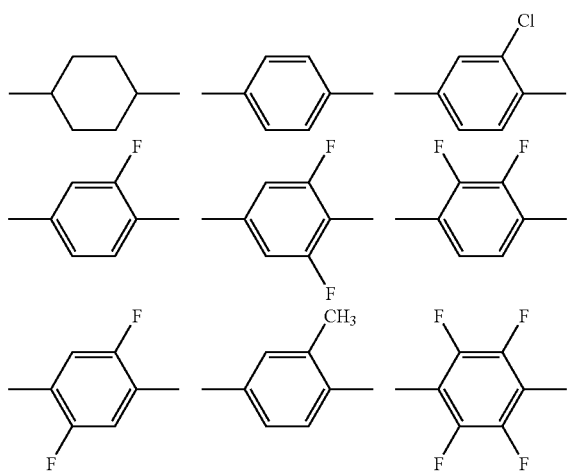

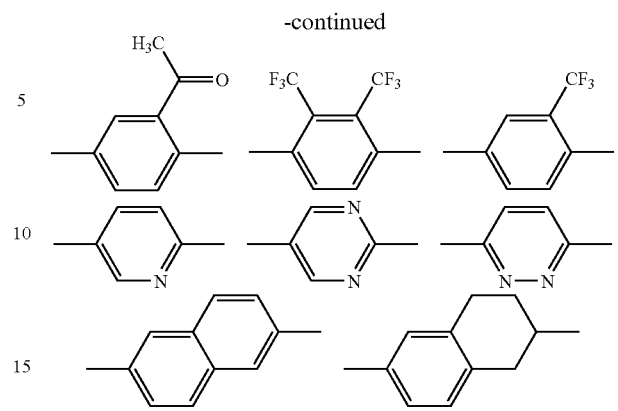

In formula (1), the cyclic structure may bond to the skeleton structure in the opposite direction in point of the right and left sides thereof. For example, the structure of 2-fluoro-1,4-phenylene is the same as that of 3-fluoro-1,4-phenylene, and therefore the latter is not exemplified herein. This rule shall apply to the relation between 2,6-difluoro-1,4-phenylene and 3,5-difluoro-1,4-phenylene. Regarding the steric configuration thereof, 1,4-cyclohexylene, if any, in the compound (1) preferably has a trans-configuration rather than a cis-configuration. The compound (1) may contain a larger amount of an isotope element such as $^2$H (deuterium) or $^{13}$C than in naturally-existing compounds, in which the isotope element does not have any significant influence on the physical properties of the compound.

In formula (1), X¹ is a linking group that bonds the liquid-crystal skeleton to the polymerizable group via the spacer, alkylene. X¹ represents a single bond, —O— or —OCO—. Preferably, X¹ is a single bond or —O—. X² and X³ each are a bonding group, independently representing a single bond, —CH=CH—COO—, —OOC—CH=CH—, —CH₂CH₂—COO—, —OOC—CH₂CH₂—, —COO—, —OCO—, —OCH₂—, —CH₂O—, —OCF₂—, —CF₂O—, —CH₂CH₂—, —C≡C—, —NHCO—, or —CONH—. Their preferred examples are a single bond, —CH=CH—COO—, —CH₂CH₂—COO—, —COO—, —C≡C— and —CONH—. Suitably selecting the bonding groups makes it possible to control the phase transition temperature and the optical anisotropy of the compound. Concretely, the single bond therein may make the compound have a rigid liquid-crystal skeleton structure, and the compound may have a high clear point; —COO— may make the compound have a flexible liquid-crystal skeleton structure, and the compound may have a broad liquid-crystal temperature range; —C≡C— may make the compound have a large optical anisotropy.

—(CH₂)ₘ— is a spacer, and m indicates an integer of from 0 to 20. When m is small, then the compound may have a high clear point; but when m is large, then the compound may have a low melting point. Preferably, m is an integer of from 0 to 15, more preferably from 0 to 10, even more preferably from 0 to 8.

Suitably selecting the ring, the branch, the spacer, the linking group, the bonding group and the polymerizable group makes it possible to obtain the compound (1) having the intended physical properties.

Methods for producing the compound (1) are described. First described is a method for producing a compound (1) where $R^1$ is an alkyl group having from 1 to 5, $X^1$ is —O—, and $X^2$ is —COO—. An oxetane derivative [a] is etherified with [b] in the presence of a suitable base to give [c]. Examples of the base are potassium hydroxide, sodium hydroxide, potassium carbonate, sodium hydride. [c] is etherified with a hydroxybenzoate in the presence of a suitable base to give [d]. [d] is hydrolyzed to give [e]. [e] is esterified with [f] to give the compound (1).

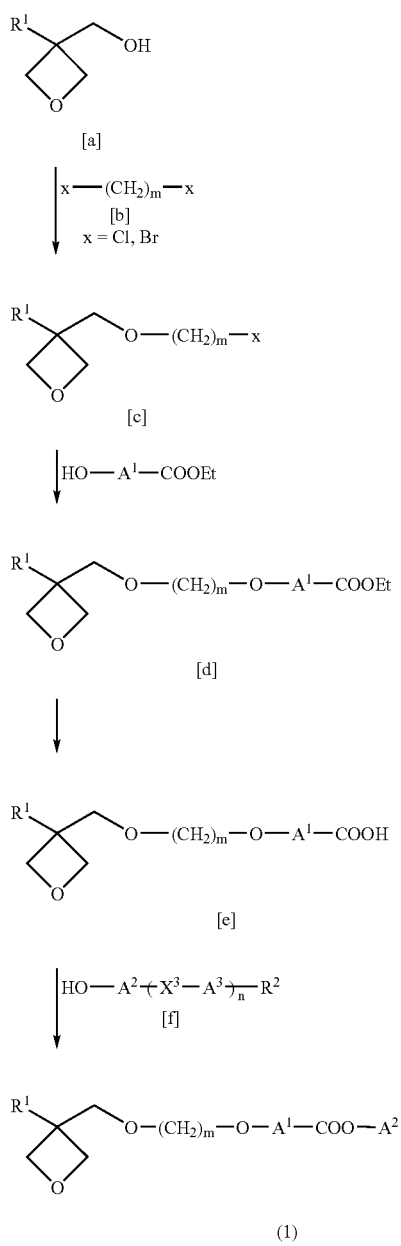

Next described is a method for producing a compound (1) where $R^1$ is an alkyl group having from 1 to 5, $X^1$ is —O—, and $X^2$ is —CONH—. A benzoic acid derivative [e] is chlorinated with a chlorinating agent such as thionyl chloride to give its corresponding acid chloride. The acid chloride is amidated with an aniline derivative [g] to give the compound (1).

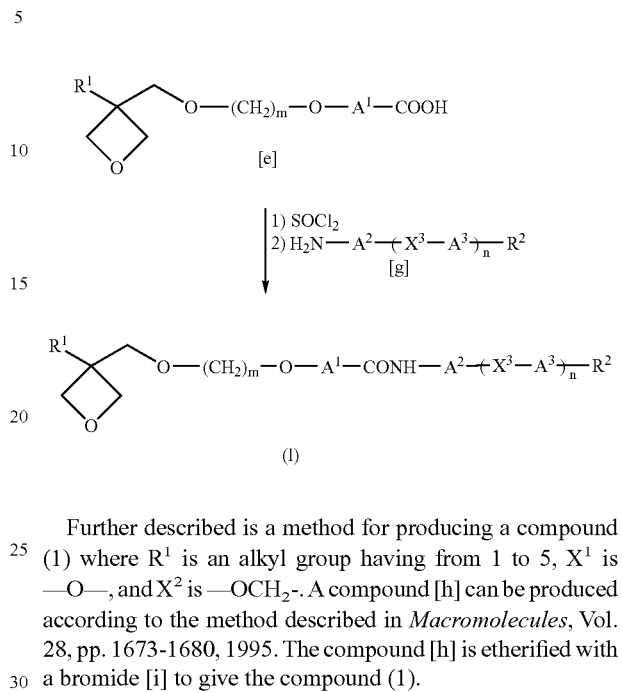

Further described is a method for producing a compound (1) where $R^1$ is an alkyl group having from 1 to 5, $X^1$ is —O—, and $X^2$ is —OCH$_2$-. A compound [h] can be produced according to the method described in *Macromolecules*, Vol. 28, pp. 1673-1680, 1995. The compound [h] is etherified with a bromide [i] to give the compound (1).

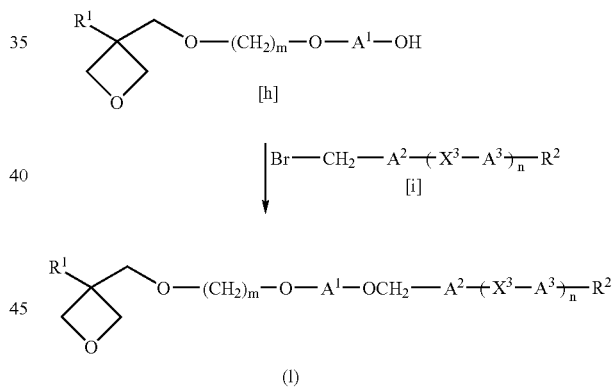

Further described is a method for producing a compound (1) where $R^1$ is an alkyl group having from 1 to 5, $X^1$ is —O—, and $X^2$ is a single bond. [c] is etherified with a phenol derivative [j] to give a bromide [k]. [k] is cross-coupled with a boronic acid derivative [l] to give the compound (1).

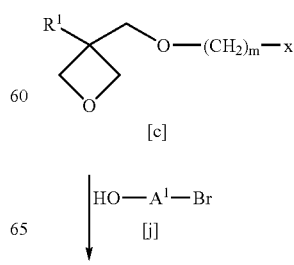

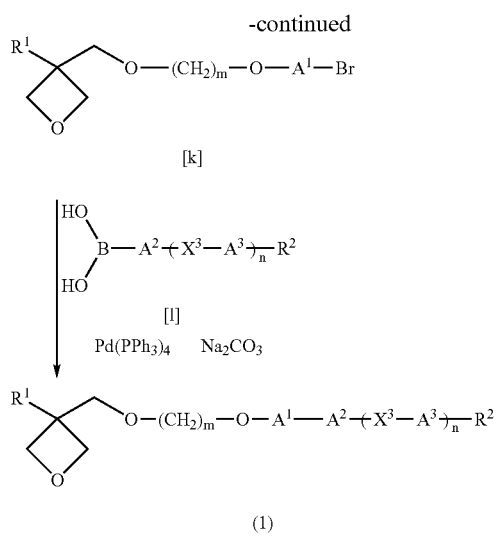

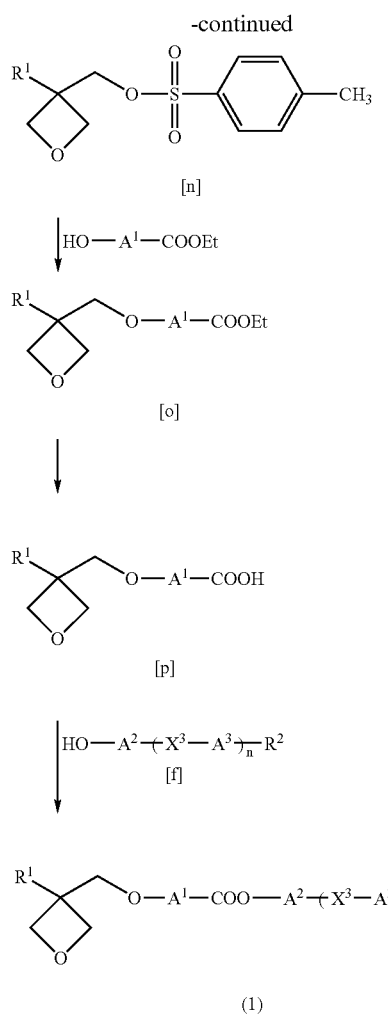

Further described is a method for producing a compound (1) where $R^1$ is an alkyl group having from 1 to 5, $X^1$ is a single bond, m=0, and $X^2$ is —COO—. An oxetane derivative [a] is tosylated with a p-toluenesulfonyl chloride [m] in the presence of a base such as pyridine to give [n]. [n] is etherified with a hydroxybenzoate derivative in the presence of a suitable base to give [o]. [o] is hydrolyzed to give [p]. [p] is esterified with [f] to give the compound (1).

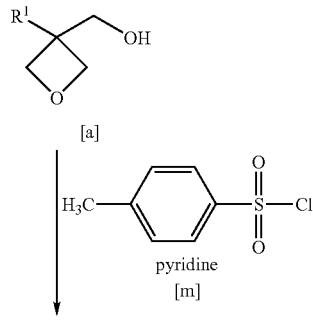

Compounds Nos. 1 to 125 that can be produced according to the above-mentioned methods are mentioned below.

No. 1 to No. No. 125

No. 1

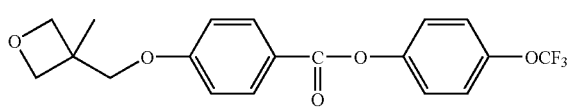

No. 2

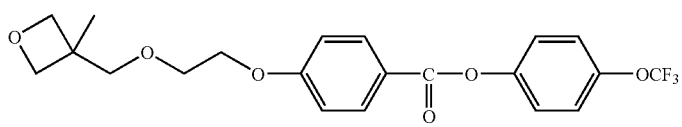

No. 3

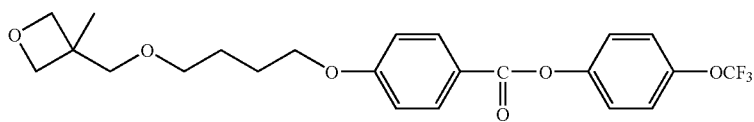

-continued
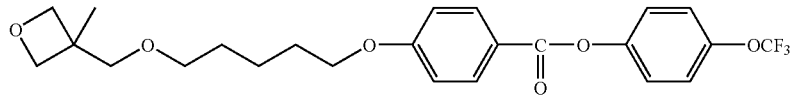
No. 4
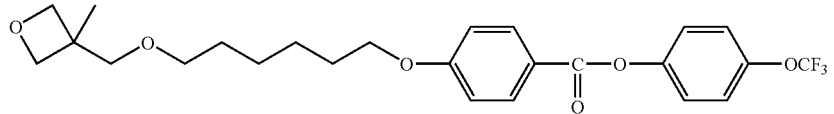
No. 5
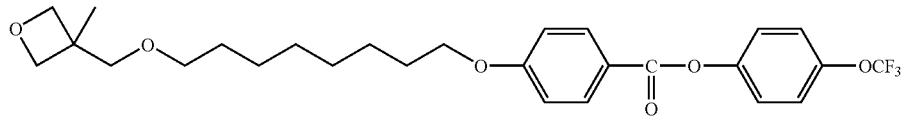
No. 6
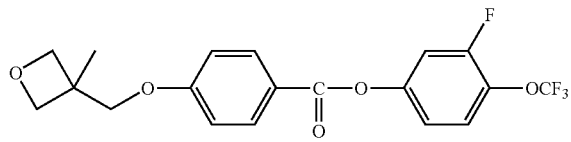
No. 7
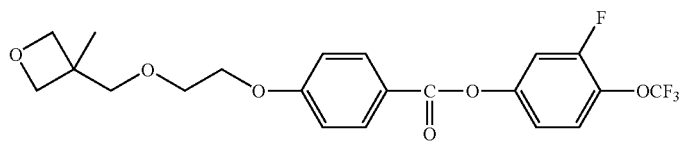
No. 8
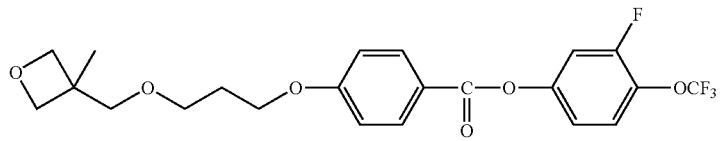
No. 9
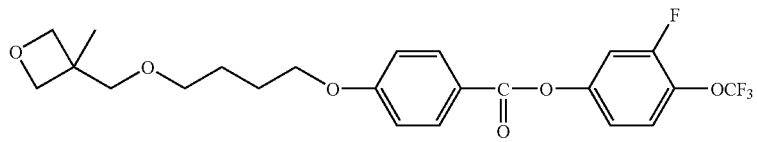
No. 10
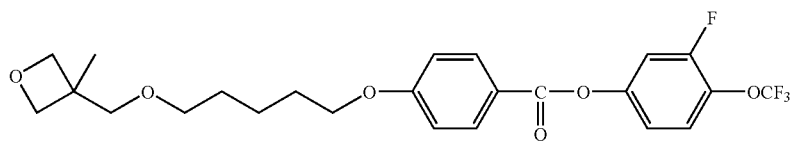
No. 11
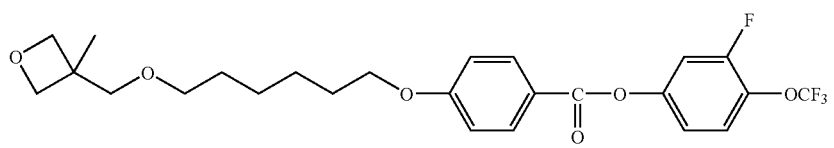
No. 12
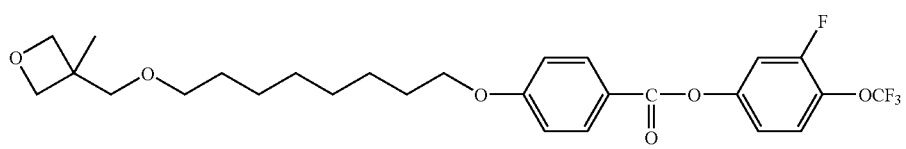
No. 13
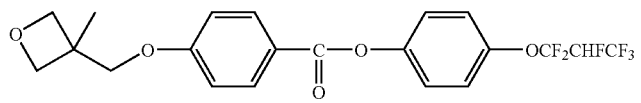
No. 14

-continued
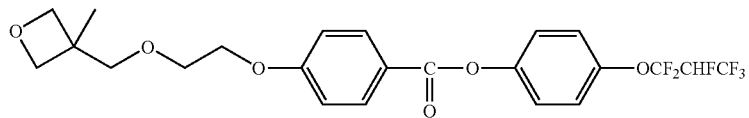
No. 15
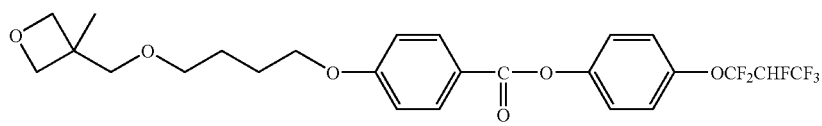
No. 16
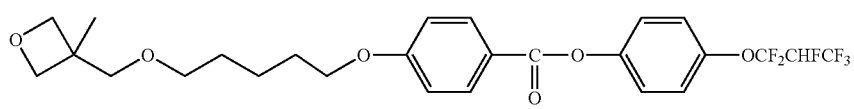
No. 17
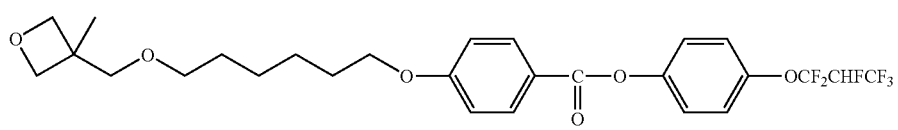
No. 18
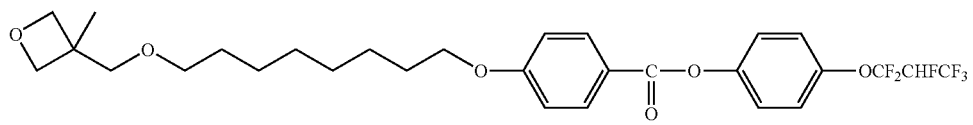
No. 19
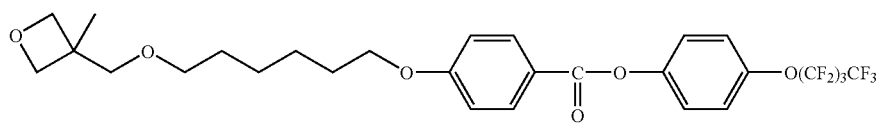
No. 20
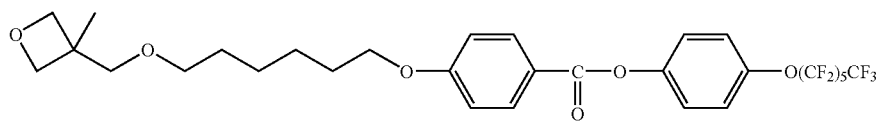
No. 21
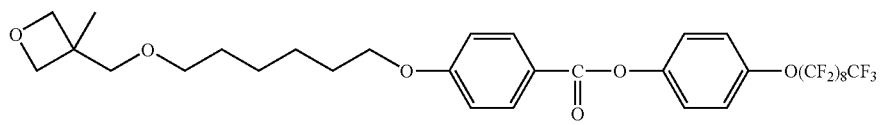
No. 22
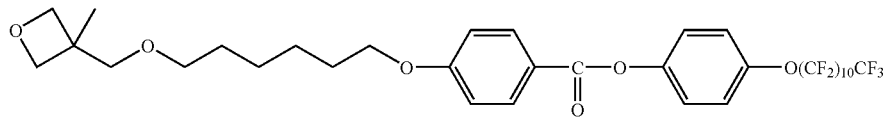
No. 23
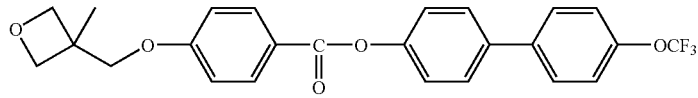
No. 24
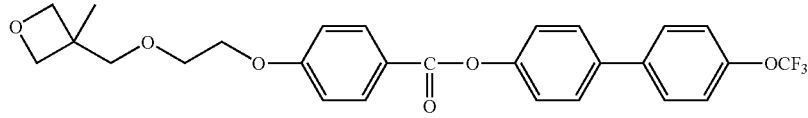
No. 25
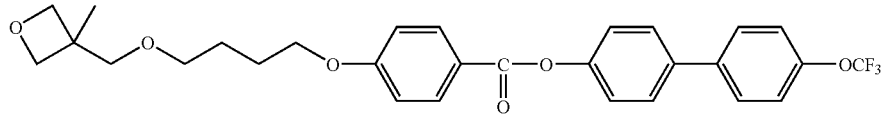
No. 26
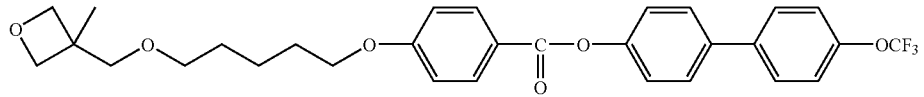
No. 27

-continued
No. 28
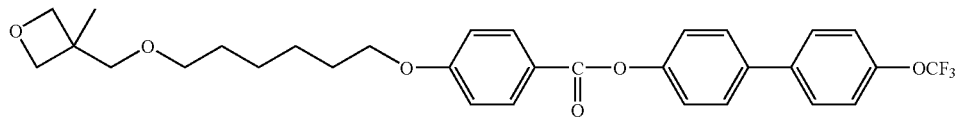
No. 29
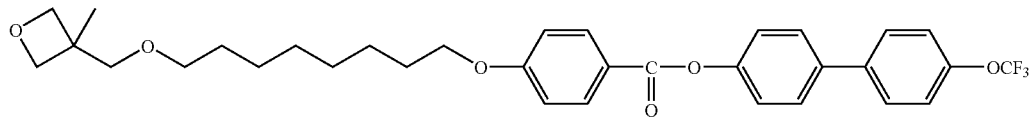
No. 30
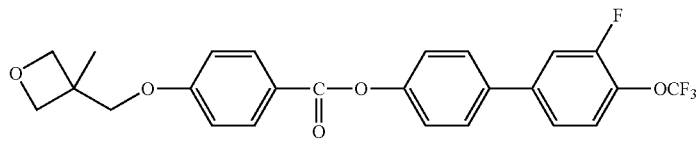
No. 31
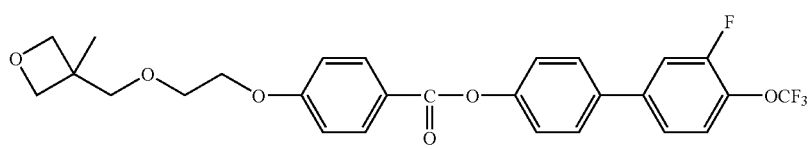
No. 32
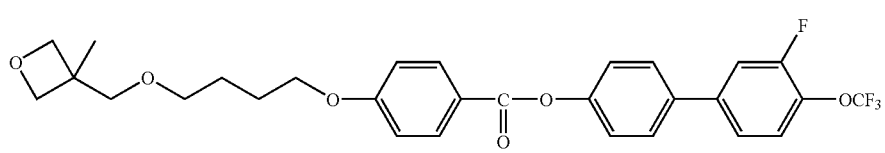
No. 33
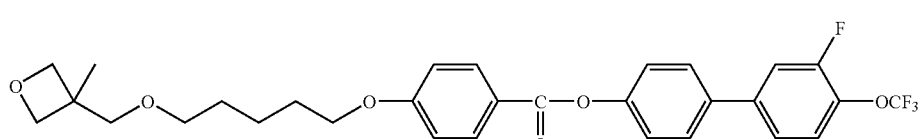
No. 34
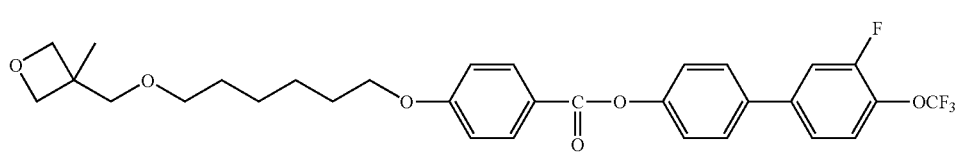
No. 35
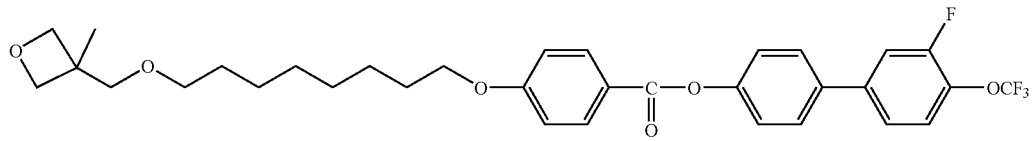
No. 36
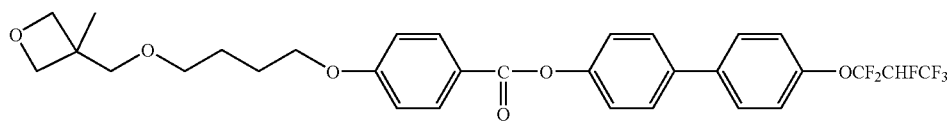
No. 37
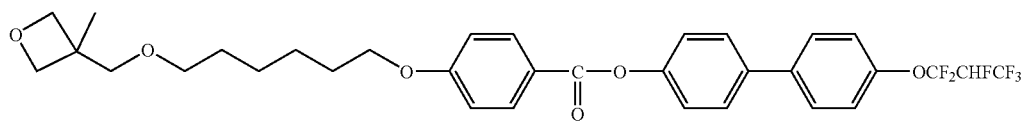
No. 38
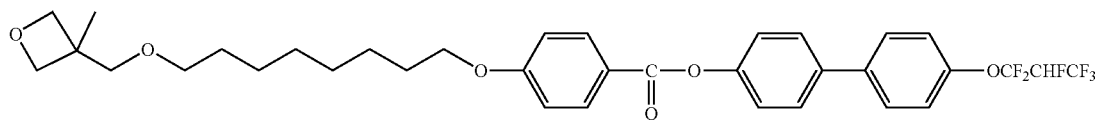

-continued
No. 39
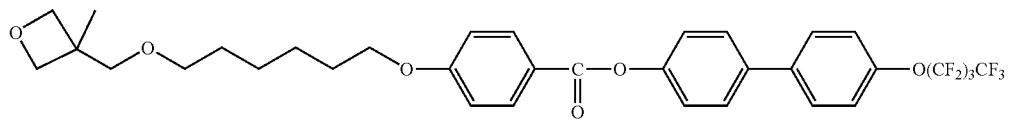
No. 40
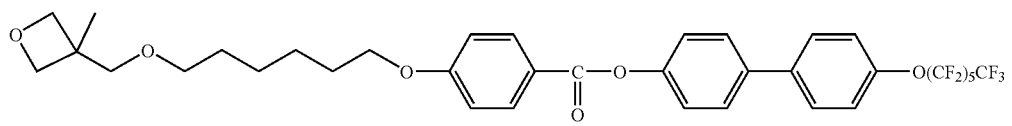
No. 41
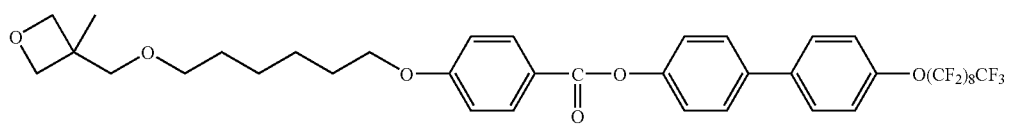
No. 42
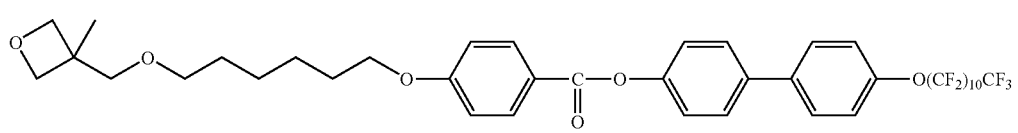
No. 43
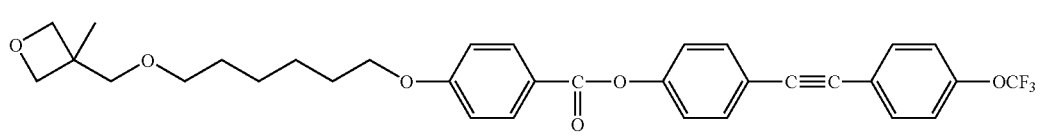
No. 44
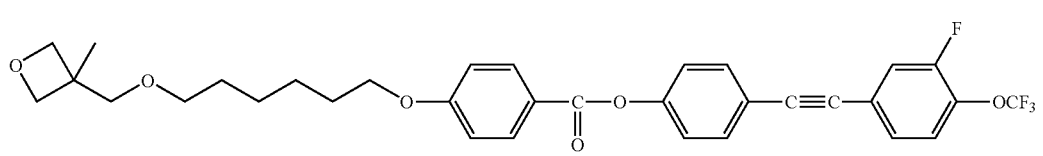
No. 45
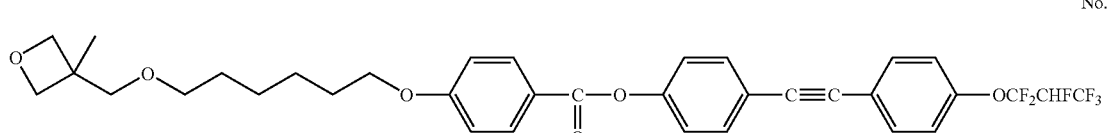
No. 46
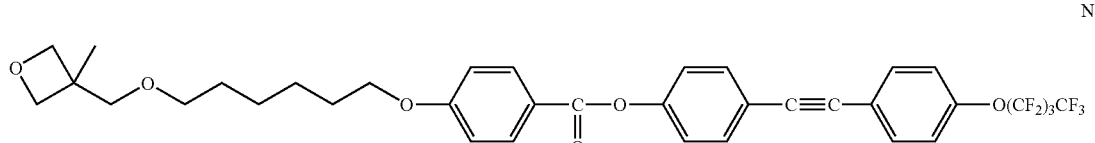
No. 47
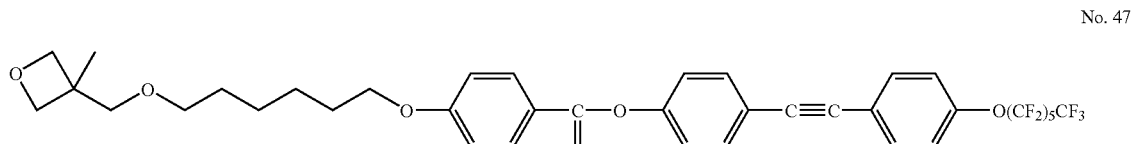
No. 48
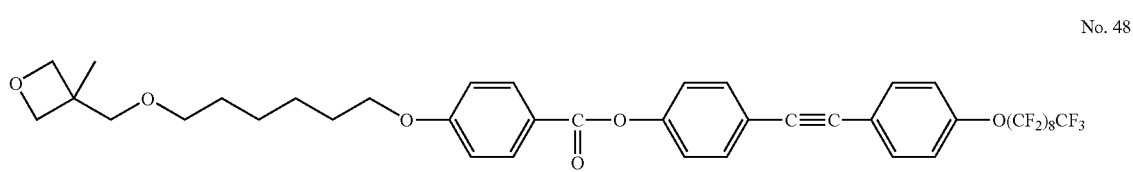

-continued
No. 49
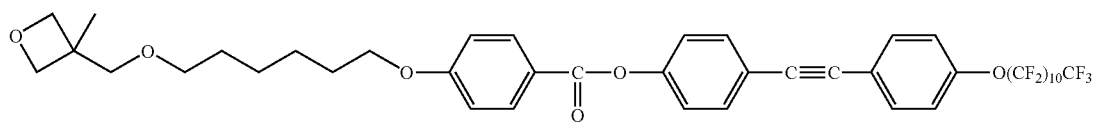
No. 50
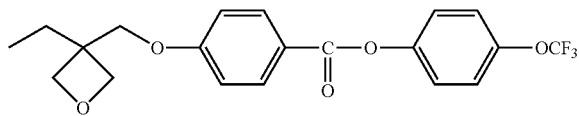
No. 51
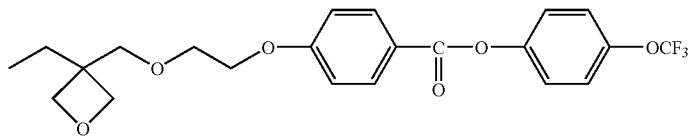
No. 52
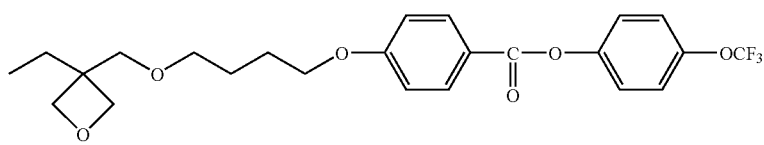
No. 53
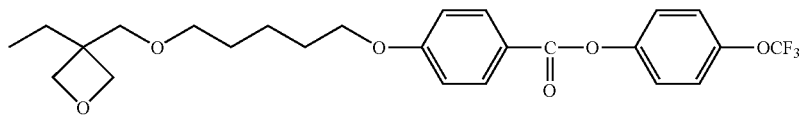
No. 54
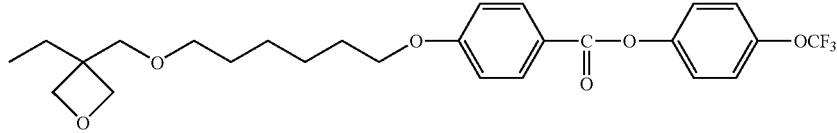
No. 55
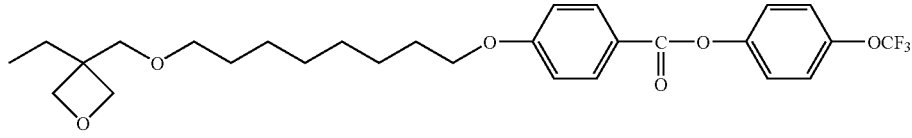
No. 56
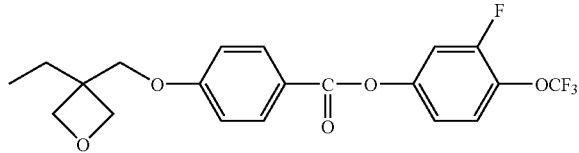
No. 57
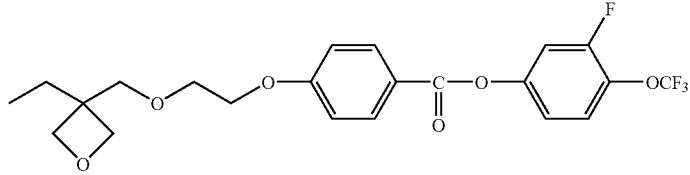
No. 58
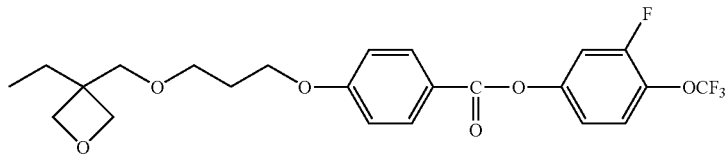

-continued
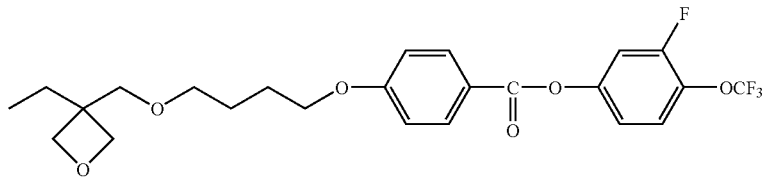
No. 59
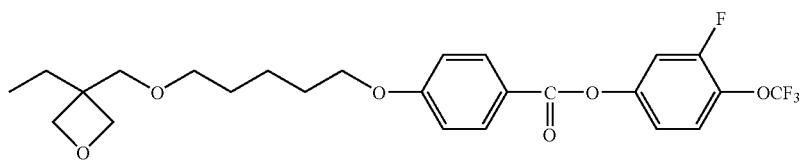
No. 60
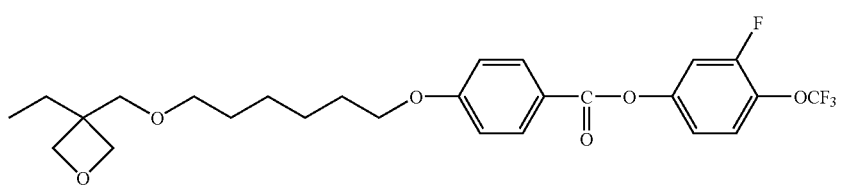
No. 61
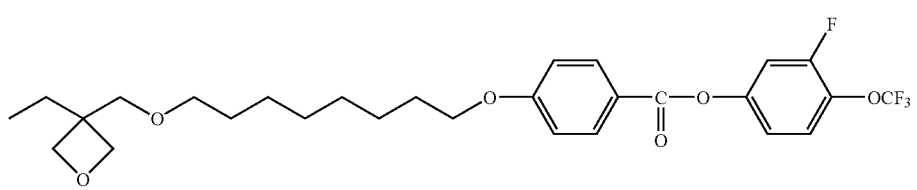
No. 62
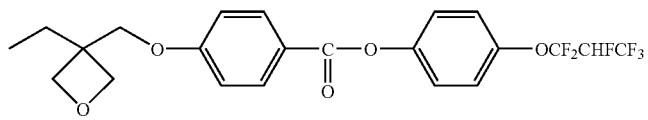
No. 63
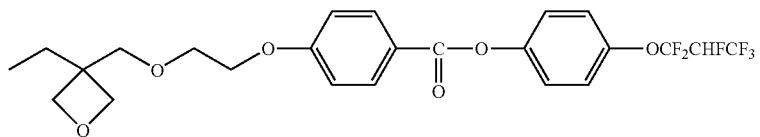
No. 64
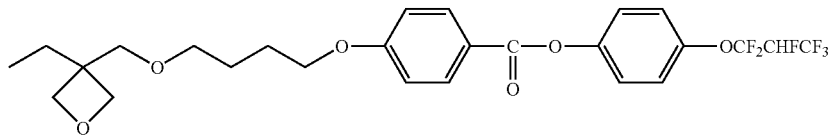
No. 65
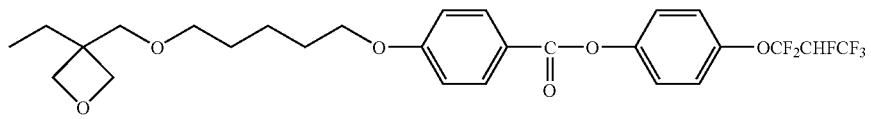
No. 66
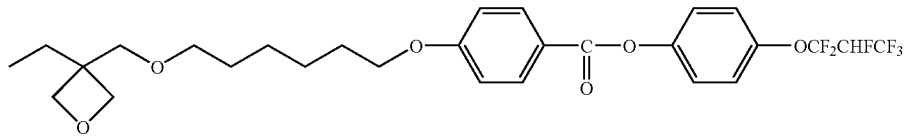
No. 67
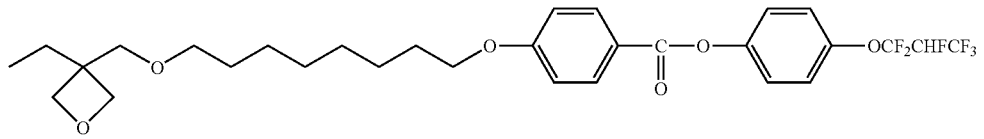
No. 68

-continued
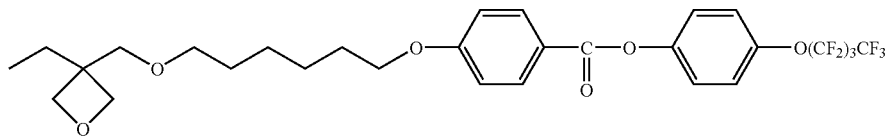
No. 69
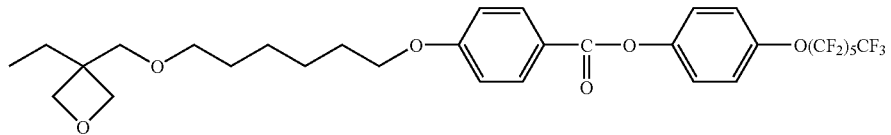
No. 70
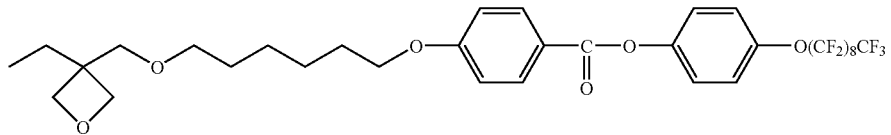
No. 71
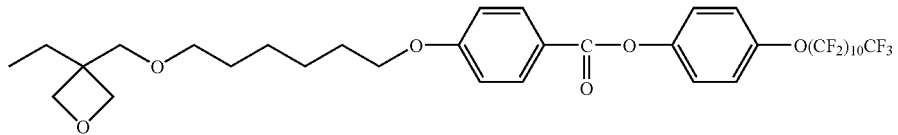
No. 72
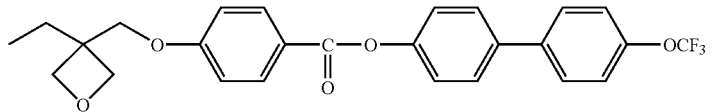
No. 73
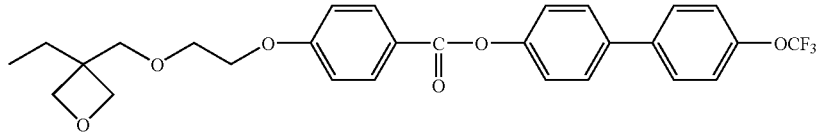
No. 74
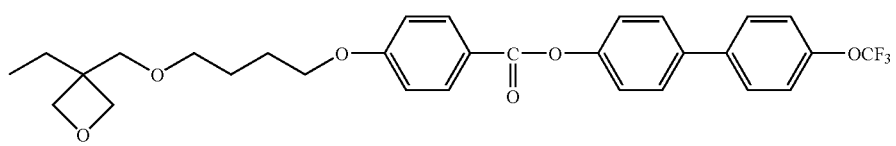
No. 75
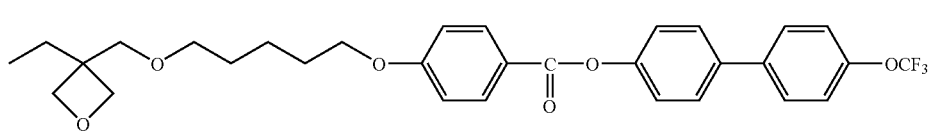
No. 76
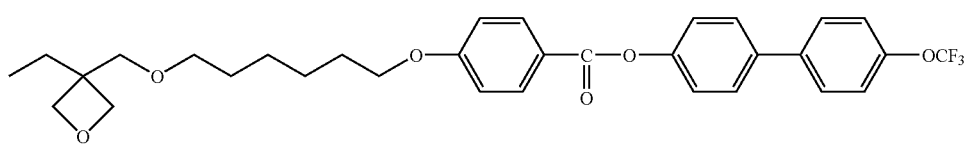
No. 77
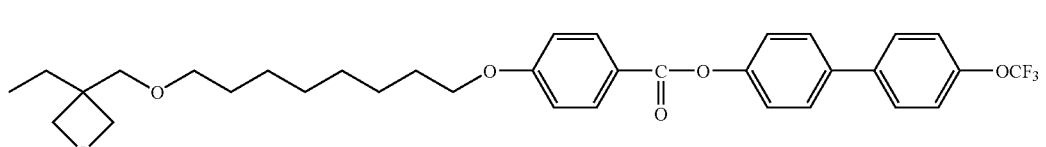
No. 78

-continued
No. 79
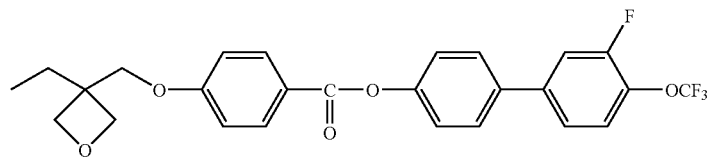
No. 80
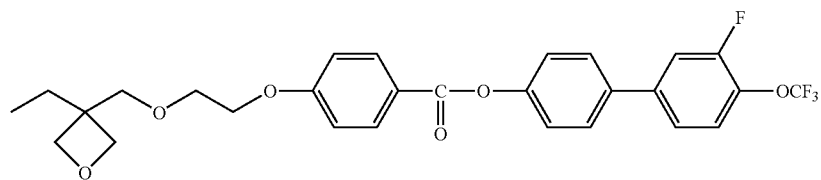
No. 81
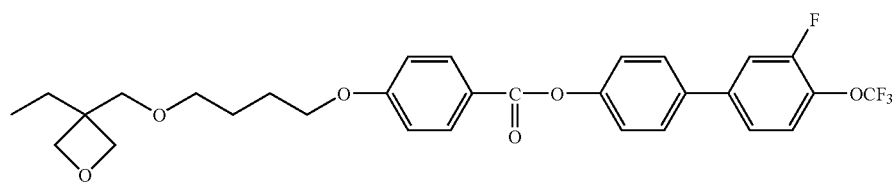
No. 82
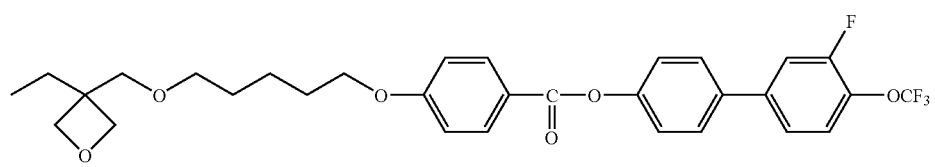
No. 83
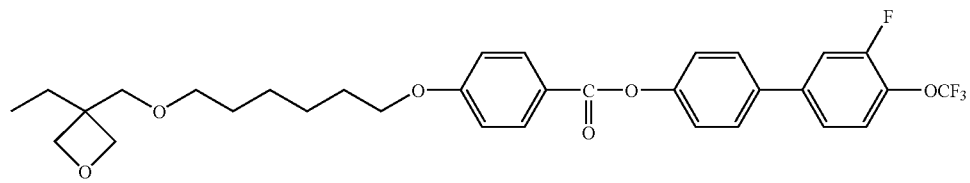
No. 84
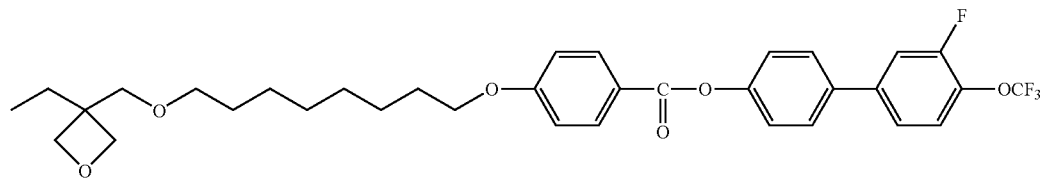
No. 85
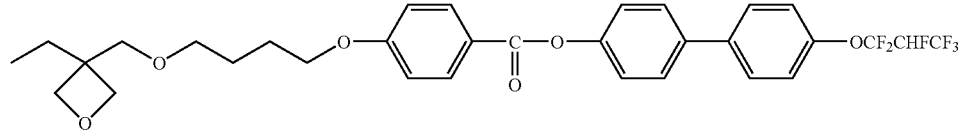
No. 86
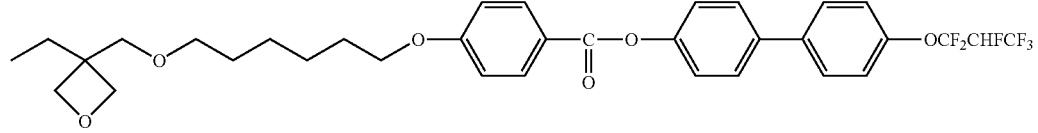
No. 87
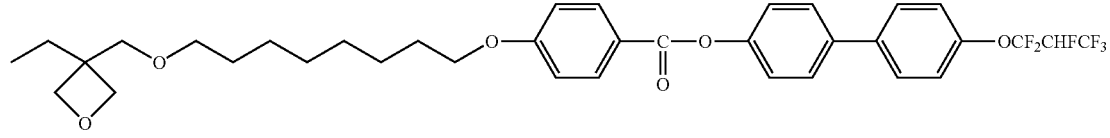

-continued
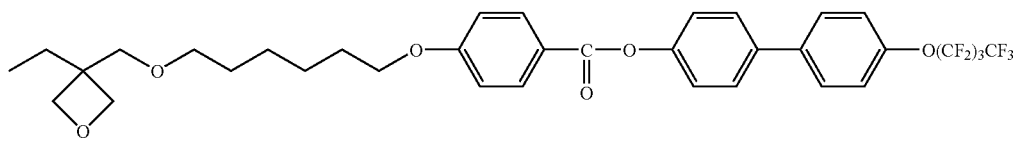
No. 88
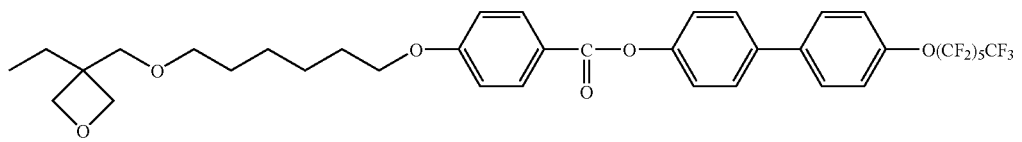
No. 89
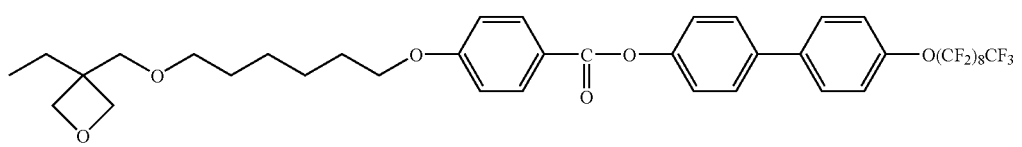
No. 90
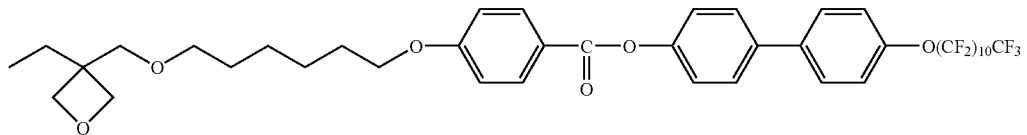
No. 91
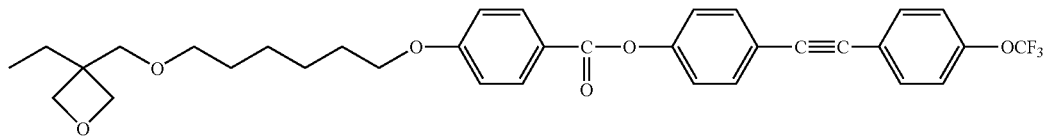
No. 92
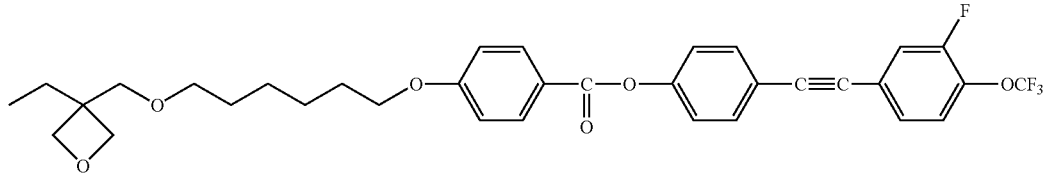
No. 93
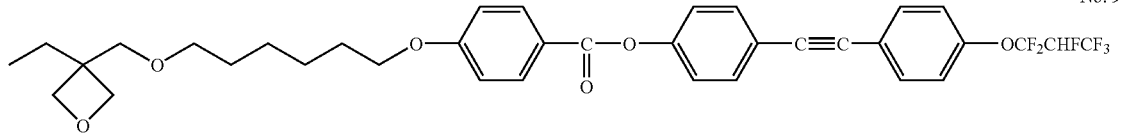
No. 94
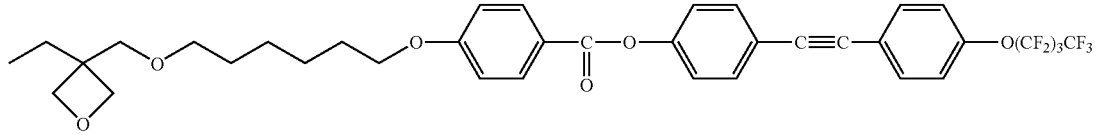
No. 95
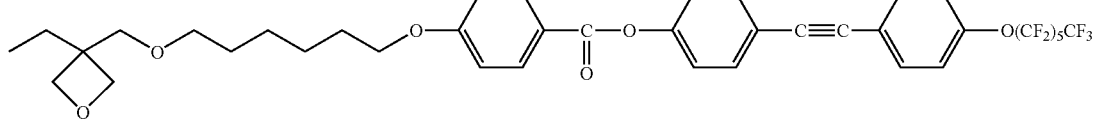
No. 96
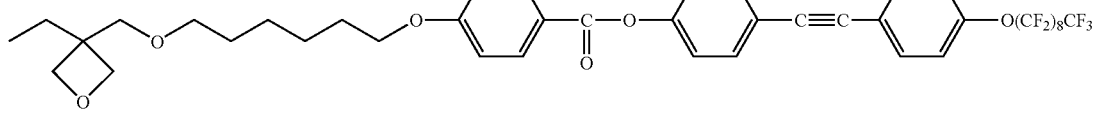
No. 97

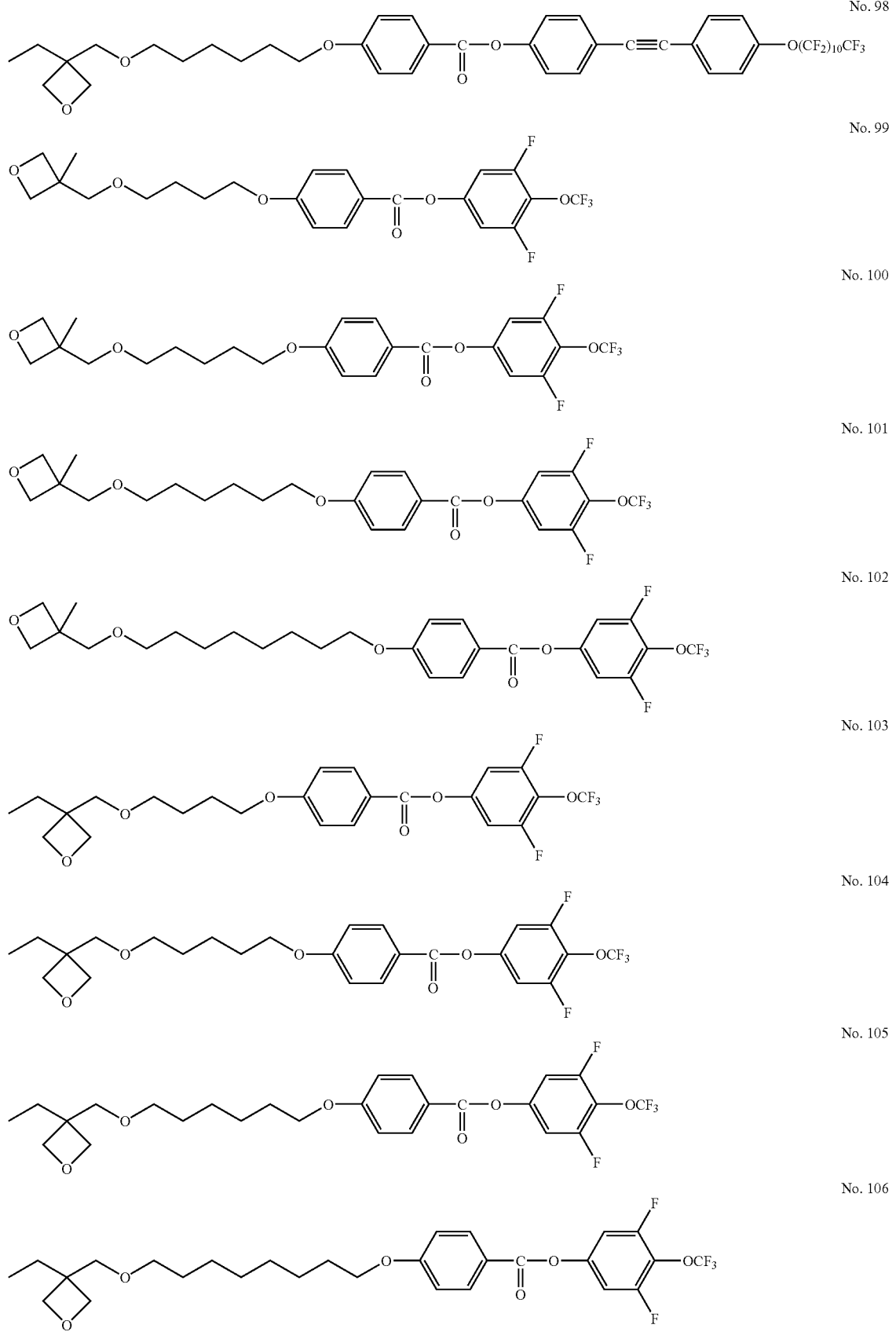

-continued
No. 107
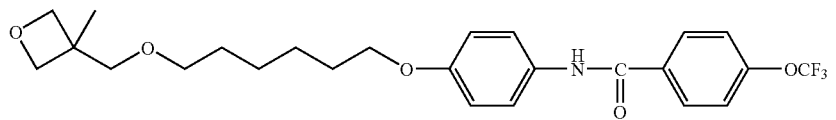
No. 108
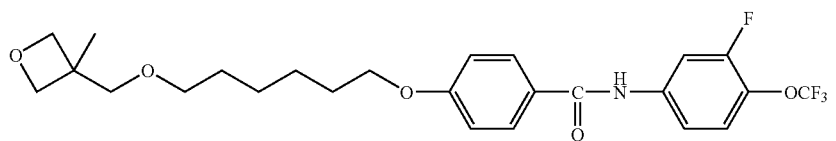
No. 109
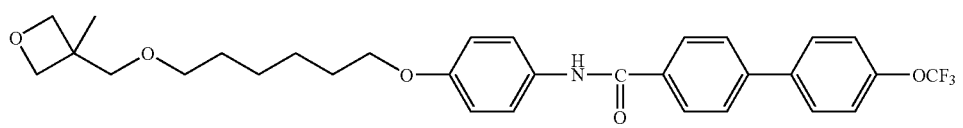
No. 110
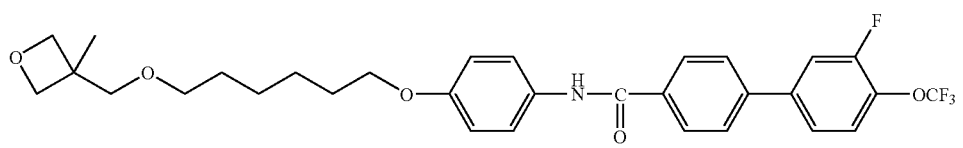
No. 111
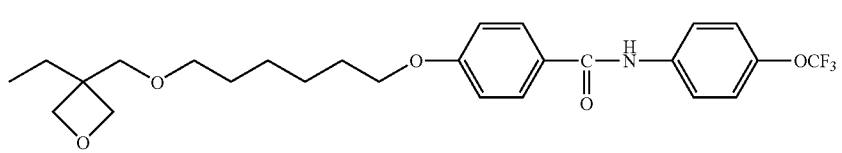
No. 112
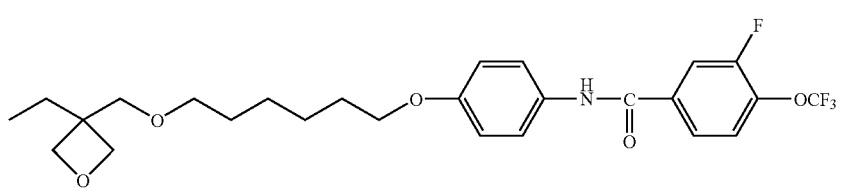
No. 113
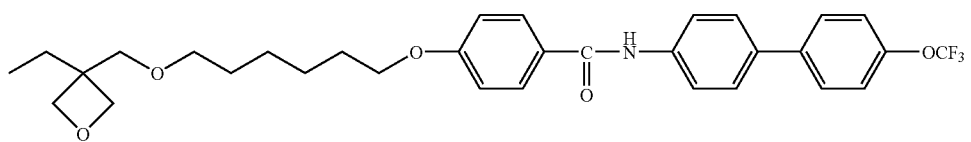
No. 114
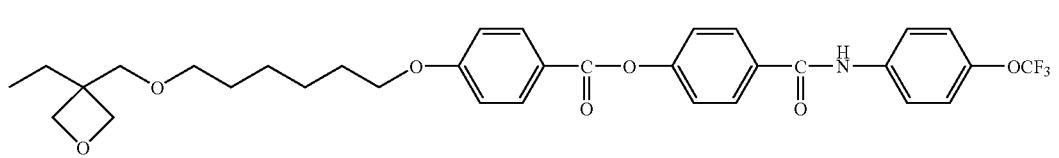
No. 115
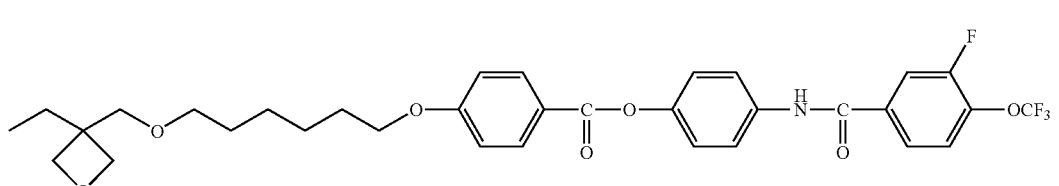
No. 116
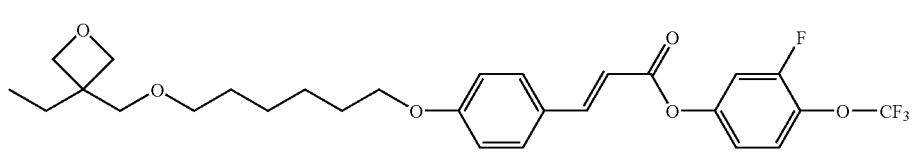

-continued
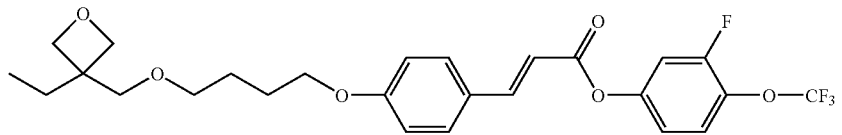
No. 117
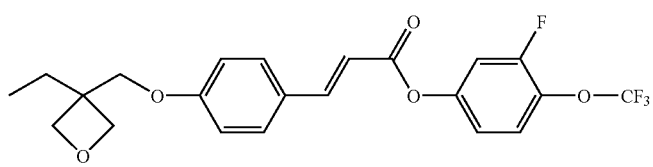
No. 118
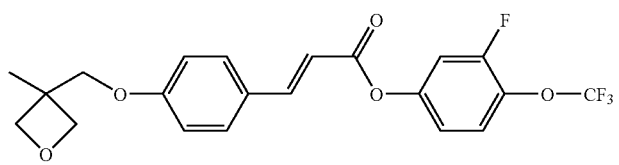
No. 119
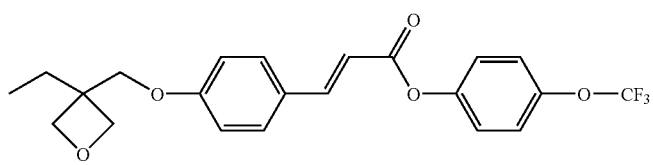
No. 120
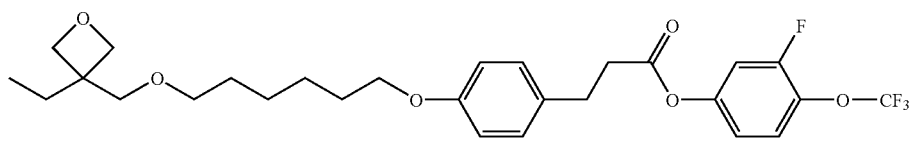
No. 121
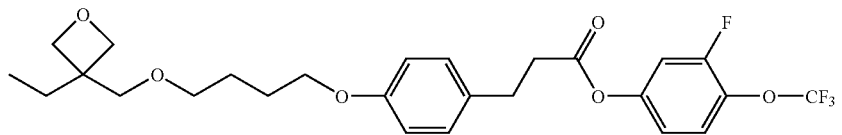
No. 122
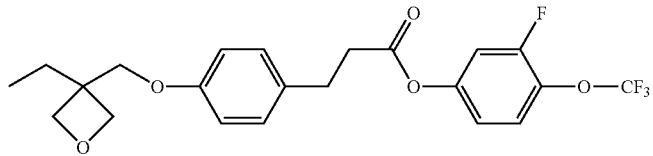
No. 123
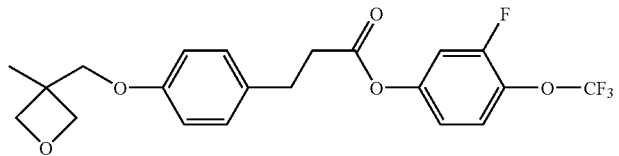
No. 124
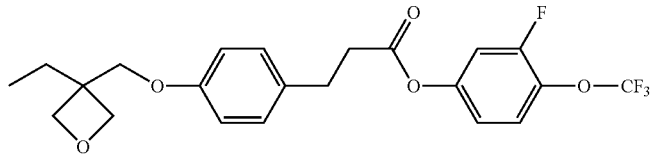
No. 125

The composition is characterized by the following:

(1) As comprising a liquid-crystal compound having a group of high polymerization reactivity, such as an oxetanyl or oxiranyl group, the composition undergoes rapid polymerization through exposure to electron rays such as UV rays in the presence of a suitable photocationic polymerization initiator added thereto.

(2) The composition has good orientation capability.

(3) The composition is compatible with any other polymerizable liquid-crystal compound.

The composition of the invention is a liquid-crystal composition containing at least two compounds, in which at least one compound is a compound of formula (1). Preferably, the liquid-crystal composition contains at least one compound of formula (1) and at least one polymerizable compound selected from a group of compounds of formulae (M1), (M2), (M3), (M4) and (M5):

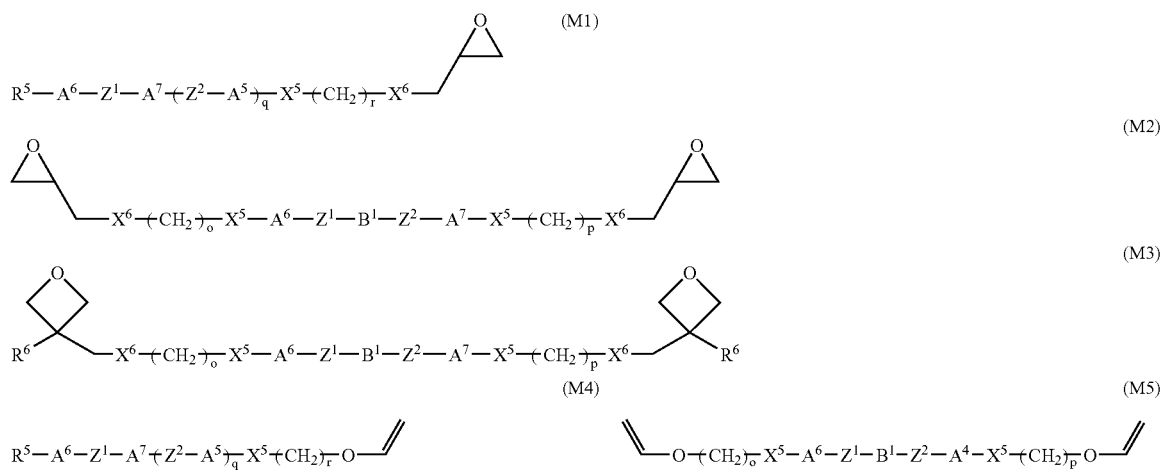

wherein $R^5$ independently represents a hydrogen atom, a fluorine atom, a chlorine atom, —CN, or an alkyl group having from 1 to 20 carbon atoms; in the alkyl group, any —CH$_2$— may be substituted with —O—, —S—, —COO—, —OCO— or —CO—, and any hydrogen may be substituted with a halogen atom; $R^6$ independently represents a hydrogen atom or an alkyl group having from 1 to 5 carbon atoms; $A^4$, $A^5$, $A^6$ and $A^7$ each independently represent a 1,4-cyclohexylene group, a 1,4-phenylene group, a pyridine-2,5-diyl group, a pyrimidine-2,5-diyl group, a naphthalene-2,6-diyl group, a fluorene-2,7-diyl group, or a 1,4-phenylene group in which any hydrogen atom is substituted with a halogen atom or a cyano group; $B^1$ independently represents a single bond, a 1,4-phenylene group, a naphthalene-2,6-diyl group, a biphenyl-4,4'-diyl group, a fluorene-2,7-diyl group, a 9-methylfluoren-2,7-diyl group, a 9-ethylfluorene-2,7-diyl group, a 9,9-dimethylfluoren-2,7-diyl group, a 9-chlorofluoren-2,7-diyl group, a 9,9-difluorofluoren-2,7-diyl group, or a 1,4-phenylene group in which any hydrogen is substituted with a halogen atom, a cyano group, a methyl group or trifluoromethyl group; $Z^1$ and $Z^2$ each independently represent a single bond, —COO—, —OCO—, —CH$_2$CH$_2$—, or —C≡C—; $X^5$ and $X^6$ each independently represent a single bond or —O—; q independently indicates 1 or 0; o, p and r each independently indicate an integer of from 0 to 20.

Of the compounds (M1), especially preferred are monofunctional liquid-crystal compounds of formulae (M1a) to (M1h):

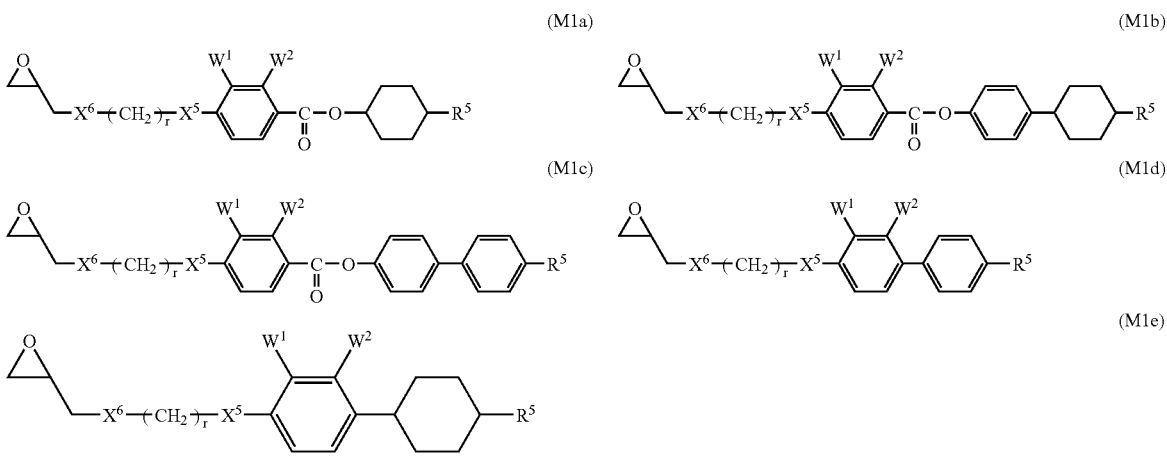

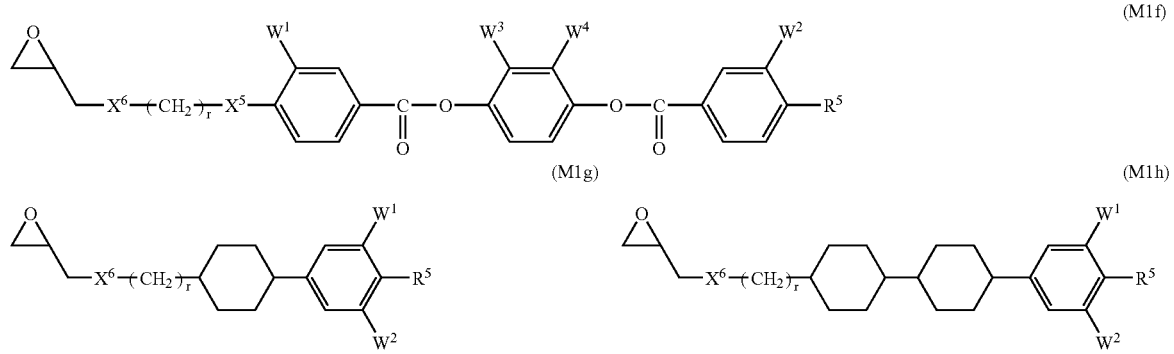
Of the compounds (M2), especially preferred are bifunctional liquid-crystal compounds of formulae (M2a) to (M2f):
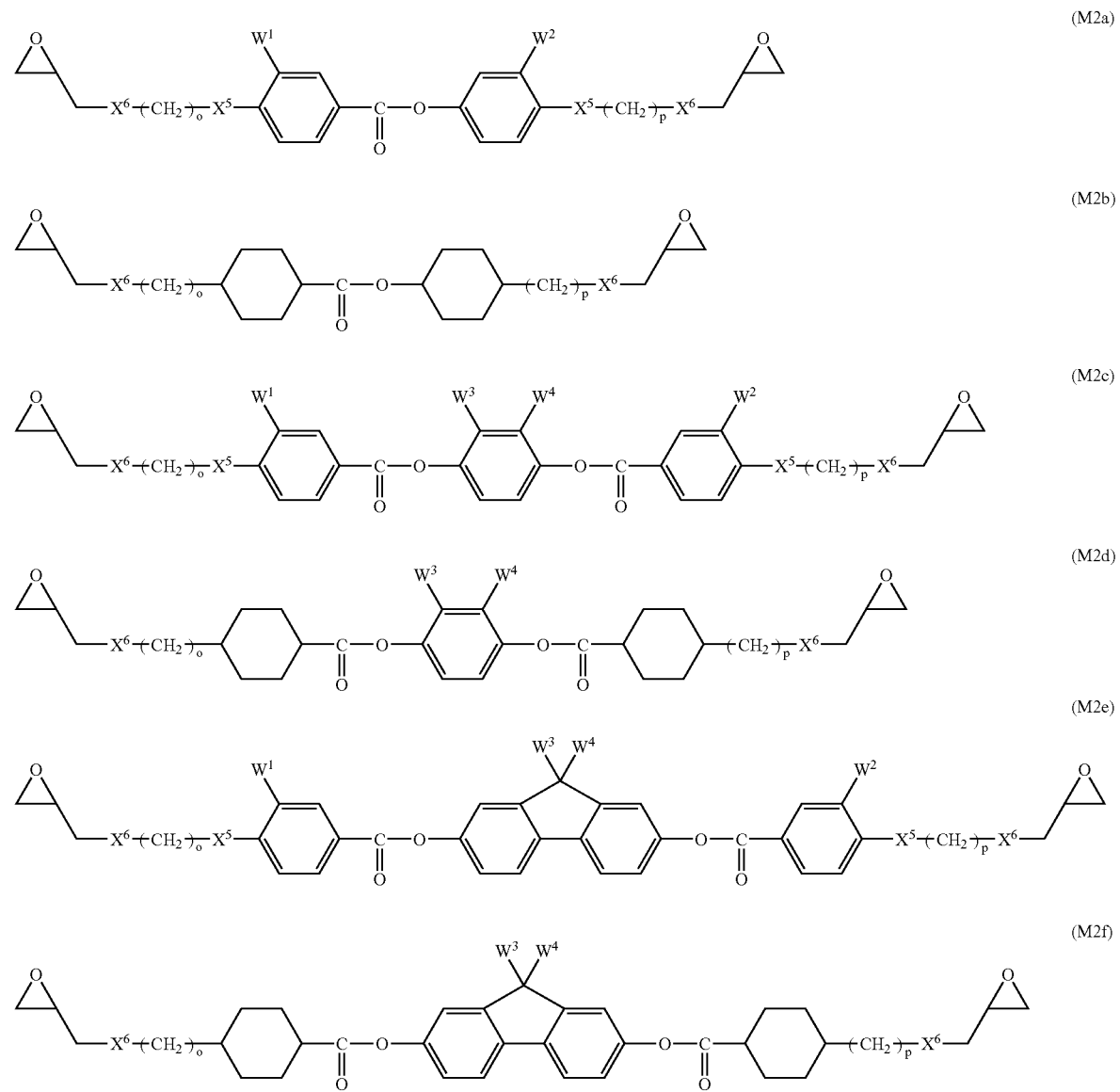

Of the compounds (M3), especially preferred are bifunctional liquid-crystal compounds of formulae (M3a) to (M3c):
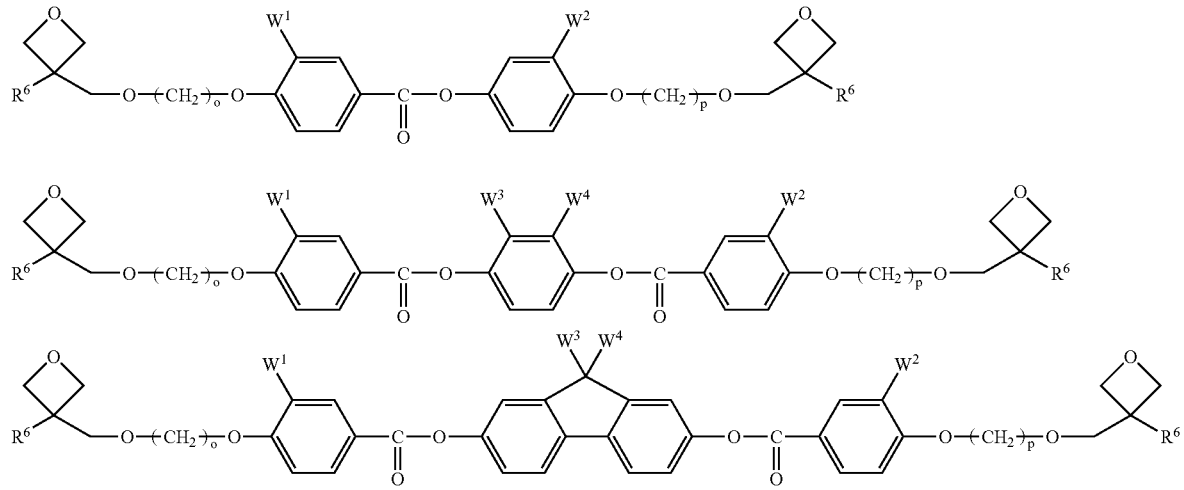
Of the compounds (M4), especially preferred are monofunctional liquid-crystal compounds of formulae (M4a) to (M4h):
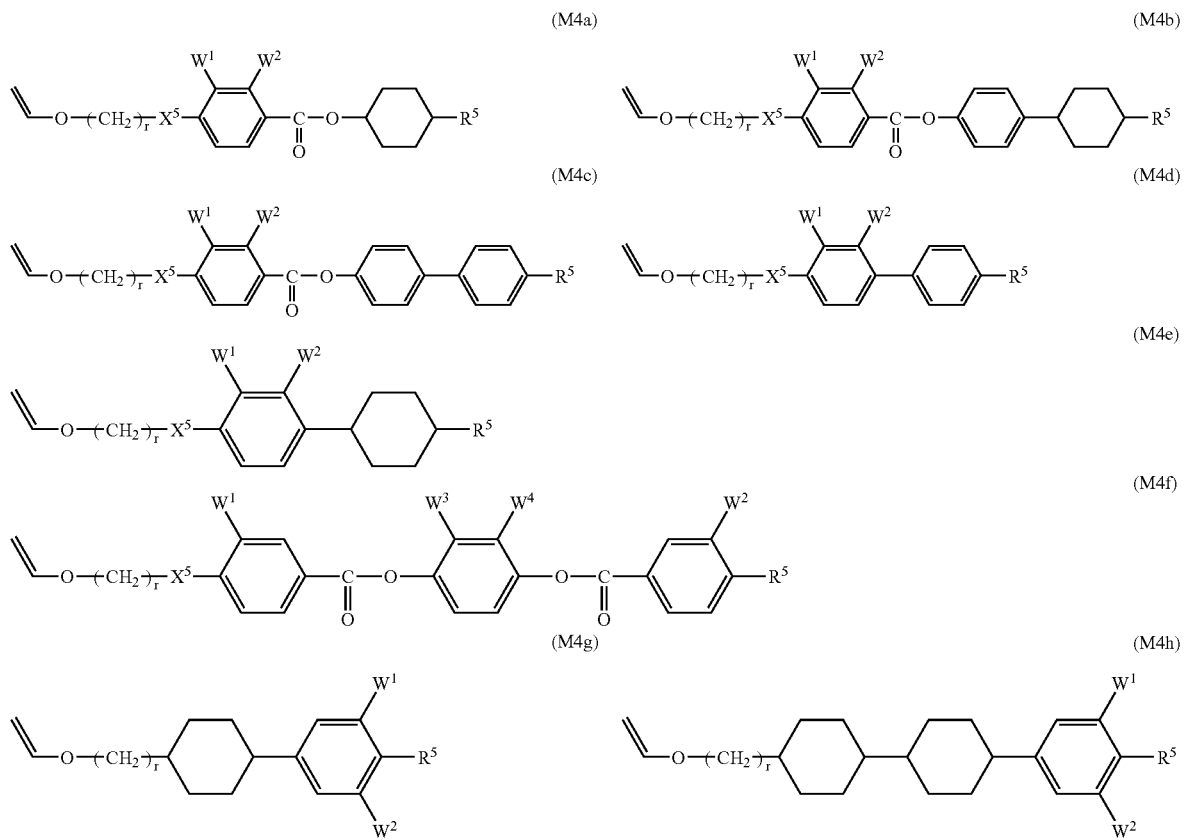

Of the compounds (M5), especially preferred are bifunctional liquid-crystal compounds of formulae (M5a) to (M5f):

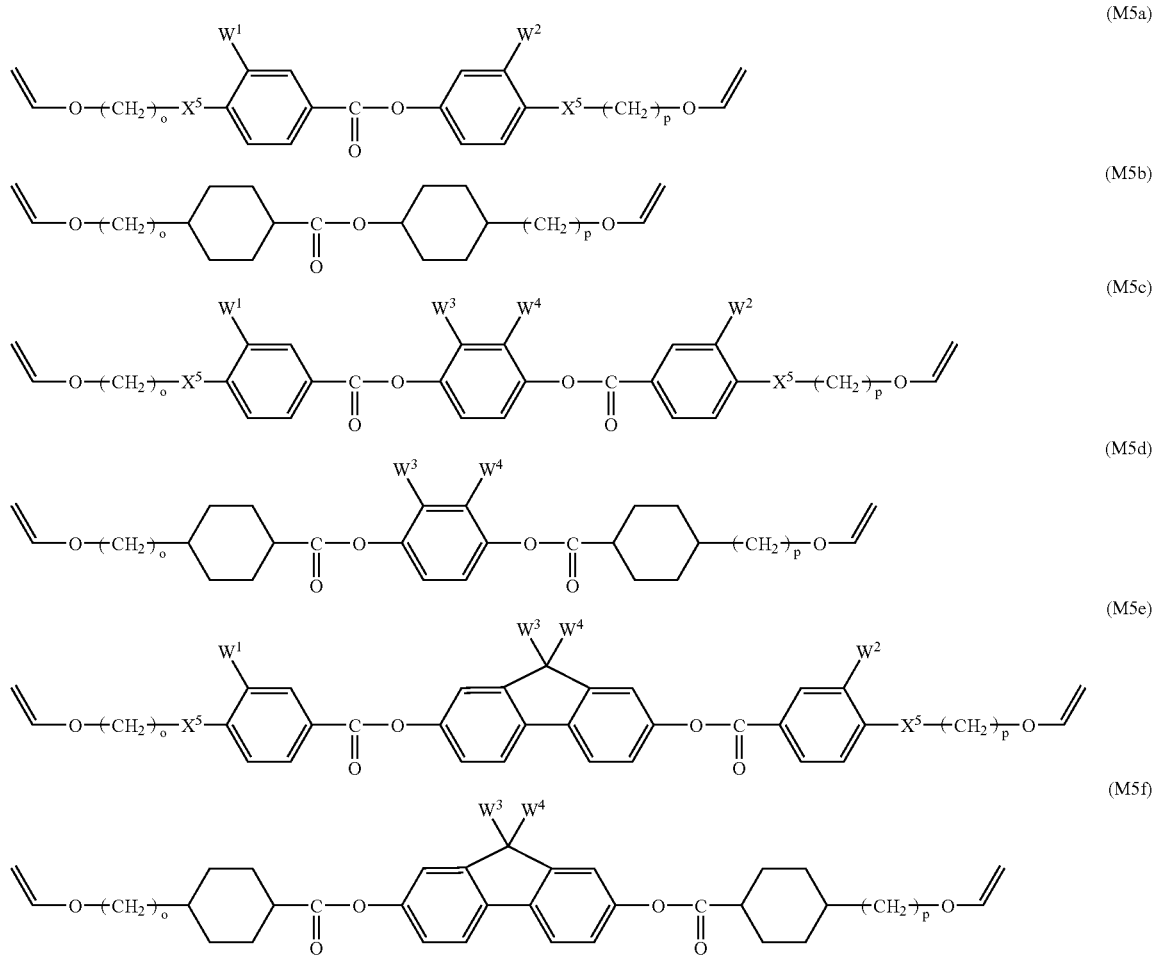

In formulae (M1a) to (M5f), $R^5$ independently represents a hydrogen atom, a fluorine atom, a chlorine atom, —CN, an alkyl group having from 1 to 20 carbon atoms, or an alkoxy group having from 1 to 19 carbon atoms; $R^6$ represents a methyl group or an ethyl group; $W^1$ and $W^2$ each independently represent a hydrogen atom, a chlorine atom a fluorine atom, or a cyano group; $W^3$ and $W^4$ each independently represent a hydrogen atom, a chlorine atom, a fluorine atom, a cyano group, a methyl group, or a trifluoromethyl group; $X^5$ represents —O—; $X^6$ independently represents a single bond or —O—; o, p and r each independently indicate an integer of from 0 to 20.

The basic constitution of the composition of the invention comprises a compound (1) and at least one compound selected from compounds (M1) to (M5), and it includes compositions (MIX1) to (MIX8).

The content of the compound selected from compounds (M1) to (M5) in the composition is preferably from 1 to 99% by weight of the composition. More preferably, the composition comprises a compound (1) and at least one compound selected from compounds (M1) and (M2), and it includes (MIX1), (MIX2) and (MIX3). One or more different types of compounds may be selected for the compound (1), the compound (M1) and the compound (M2).

(MIX1): compound (1)+compound (M1)

(MIX2): compound (1)+compound (M2)

(MIX3): compound (1)+compound (M1)+compound (M2)

The compositions (MIX1), (MIX2) and (MIX3) may rapidly polymerize at a high polymerization speed, and after irradiated with UV rays for a few seconds, they give hard and tough films of good heat resistance.

The composition (MIX4) is a composition prepared by mixing a compound (1) and a compound (M3). One or more different types of compounds may be selected for the compound (1) and the compound (M3).

(MIX4): compound (1)+compound (M3)

The films formed of the composition have the advantages of small polymerization shrinkage and good dimensional stability.

The compositions (MIX5), (MIX6) and (MIX7) are prepared by mixing a compound (1) and at least one compound selected from compounds (M4) and (M5). One or more different types of compounds may be selected for the compound (1), the compound (M4) and the compound (M5).

(MIX5): compound (1)+compound (M4)

(MIX6): compound (1)+compound (M5)

(MIX7): compound (1)+compound (M4)+compound (M5)

The films formed of the polymer obtained by polymerizing the composition are flexible.

For improving the polymerizability (especially the polymerization speed) thereof, the liquid-crystal composition preferably contains at least one compound having a polymerizable oxiranyl group and at least one compound having a polymerizable oxetanyl group. Concretely, the composition is (MIX8) that is prepared by mixing a compound (1) with compounds (M1), (M2) and (M3). One or more different types of compounds may be selected for the compound (1), the compound (M1), the compound (M2) and the compound (M3).

(MIX8): compound (1)+compound (M1)+compound (M2)+compound (M3)

The composition has good polymerizability (high polymerization speed).

For improving the physical properties thereof, the compositions (MIX1) to (MIX8) may contain any other component than the compound (1) and the compounds (M1) to (M5), such as non-polymerizable liquid-crystal compound, polymerizable or non-polymerizable optical-active compound, non-liquid-crystal polymerizable compound, polymerization initiator, solvent, surfactant, antioxidant, filler, UV adsorbent and others. So far as they may attain the object of the invention, the additives may have any structure. These additive compounds may be any known ones. The content of each additive is preferably so determined that it does not detract from the liquid-crystal property of the composition. Even when a component of the composition contains a larger amount of an isotope element than in naturally-existing compounds, the composition comprising such a component may have the same properties as those of the composition not comprising it, and the component of the type is therefore preferable in the composition of the invention.

Examples of the non-polymerizable liquid-crystal component in the group of non-polymerizable liquid-crystal compounds, and polymerizable or non-polymerizable optical-active compounds are described in a liquid-crystal compound data base LiqCryst (registered trade mark) sold by Fujitsu Kyushu Engineering.

The optical-active compound that may be added to the composition of the invention may be any one capable of inducing a helical structure and suitably miscible with the base, polymerizable liquid-crystal compound in the composition. The optical-active compound to be added may be either a polymerizable compound or a non-polymerizable compound. According to the object of the invention, it may be optimized. In consideration of the heat resistance and the solvent resistance of the composition, the optical-active compound is preferably a polymerizable compound. Especially preferred examples of the optical-active compound are the following (OP1) to (OP13), in which the carbon with * is an asymmetric carbon.

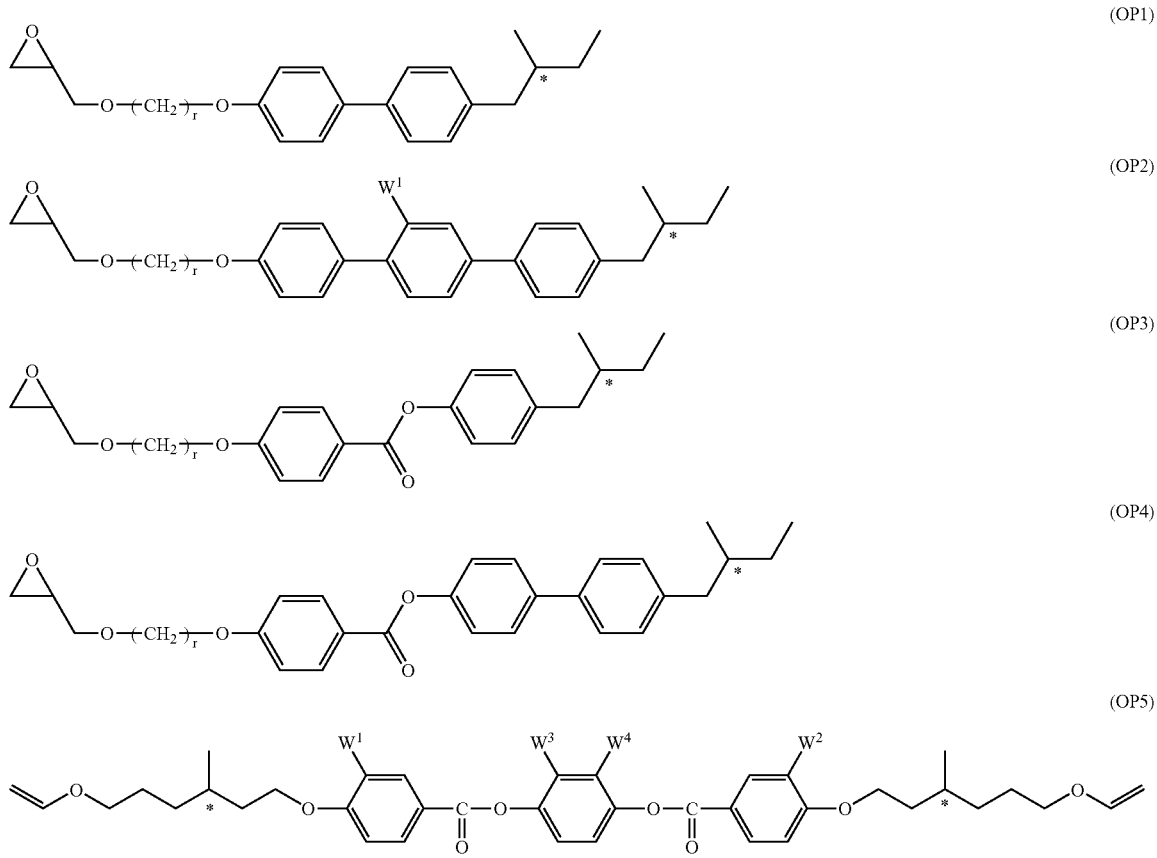

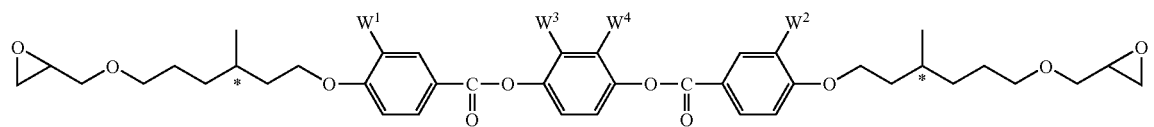
(OP6)
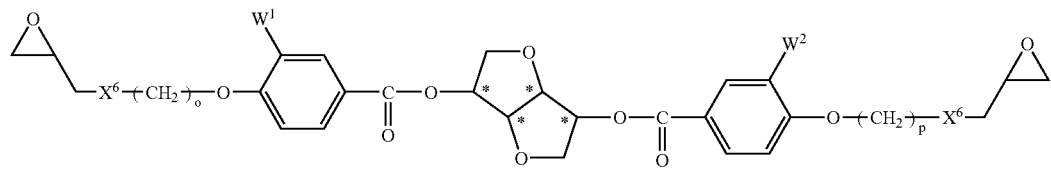
(OP7)
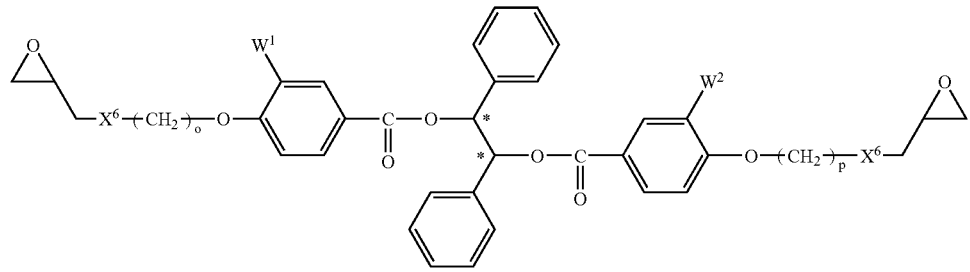
(OP8)
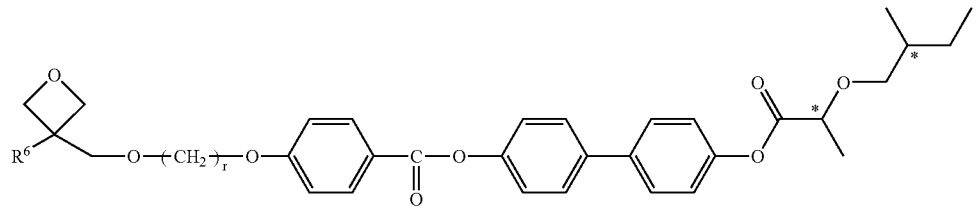
(OP9)
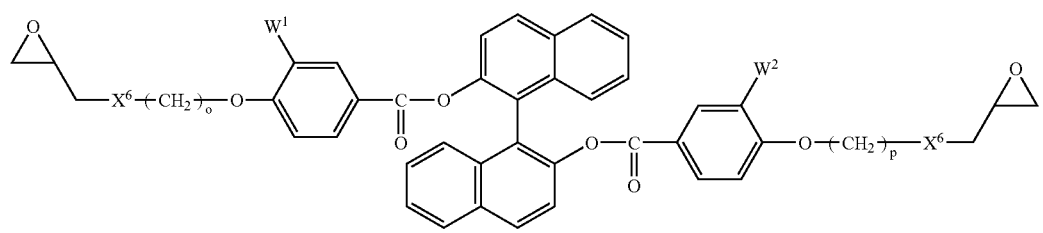
(OP10)
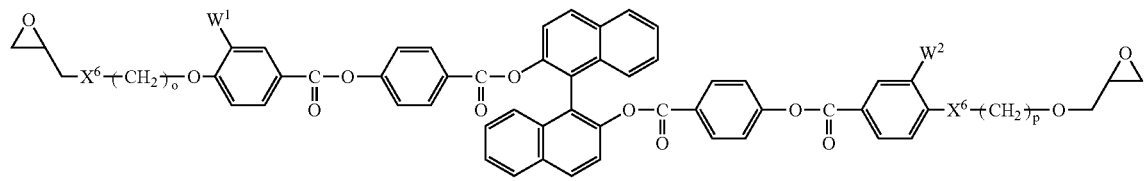
(OP11)
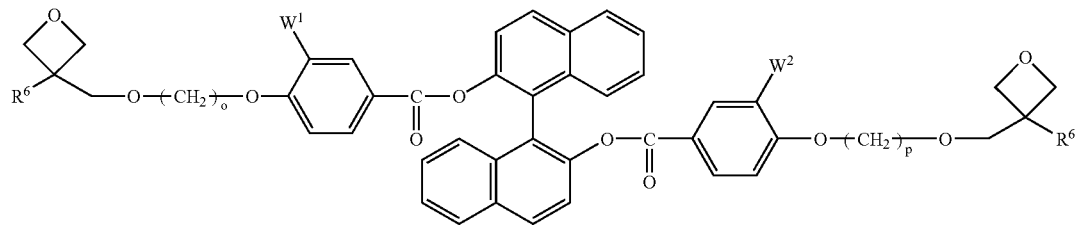
(OP12)

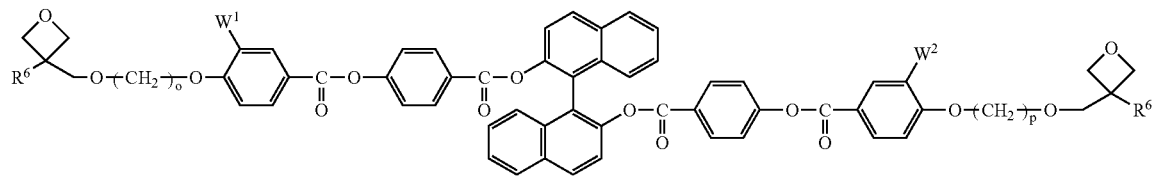

(OP13)

In these formulae (OP1) to (OP13), $R^6$ represents a methyl group or an ethyl group; $W^1$ and $W^2$ each independently represent a hydrogen atom, a chlorine atom, a fluorine atom, or a cyano group; $W^3$ and $W^4$ each independently represents a hydrogen atom, a chlorine atom, a fluorine atom, a cyano group, a methyl group, or a trifluoromethyl group; $X^6$ independently represents a single bond or —O—; o, p and r each independently indicate an integer of from 0 to 20.

The polymer of the invention is described below.

The compound (1) has a polymerizable oxetanyl group. Polymerizing the compound (1) gives the polymer of the invention. The polymer may be obtained through cationic polymerization or the like. When one compound (1) alone is polymerized, then a homopolymer is obtained. The polymer has one type of structure units. When a composition containing at least two compounds (1) is polymerized, then a copolymer is obtained. The copolymer has at least two types of structure units. The structure units constituting the copolymer may be in any form of random, block or alternate configurations. To attain the object of the invention of producing optically-anisotropic films, it is desirable that the composition is polymerized in an oriented liquid-crystal condition. Therefore, in the invention, photocationic polymerization is especially preferred.

Applications of the polymer of the invention are mentioned below.

Thermoplastic resins are usable for adhesives, mechanically-anisotropic synthetic polymers, cosmetics, decorations, non-linear optical materials and information memory materials. The thermoplastic resins for these are linear polymers not so much branched, and are obtained by polymerizing the liquid-crystal composition of the invention that comprises a monofunctional compound as the essential ingredient thereof. Preferably, the resins have a weight-average molecular weight of from 500 to 1,000,000, more preferably from 1,000 to 500,000, even more preferably from 5,000 to 100,000.

Thermosetting resins are usable for retarders, polarizing elements, liquid-crystal orientation films, antireflection films, selective reflection films and viewing angle compensatory films that are constitutive elements of liquid-crystal display devices. The thermosetting resins for these are three-dimensional network-structured polymers, and they may be obtained by polymerizing the liquid-crystal composition of the invention that gives a polymer having a high degree of polymerization. When branched more, the polymer is more hardly soluble in solvent and its hardness is higher. The molecular weight of the polymer is difficult to measure and is therefore difficult to define. Preferably, it is infinite.

For controlling the film formability and the mechanical strength thereof, the composition may contain a non-liquid-crystal polymerizable compound added thereto. Preferred examples of the non-liquid-crystal polymerizable compound are vinyl ether compounds, epoxy compounds and oxetane compounds.

Preferred examples of the non-liquid-crystal polymerizable compound that may be added to the compositions (MIX1) to (MIX8) of the invention are ethyl vinyl ether, hydroxybutyl monovinyl ether, t-amyl vinyl ether, cyclohexanedimethanolmethyl vinyl ether, and, for composition viscosity control or for polymerization shrinkage reduction, 3-ethyl-3-hydroxymethyloxetane, 3-methyl-3-hydroxymethyloxetane, di(3-ethyl-oxetan-3-ylmethyl), 3-ethyl-3-(2-ethylhexyloxymethyl)oxetane.

For easy coating or for liquid-crystal phase orientation control, a surfactant may be added to the composition not detracting from the effect of the invention. The surfactant includes, for example, imidazolines, quaternary ammonium salts, alkylamine oxides, polyamide derivatives, polyoxyethylene-polyoxypropylene condensates, polyethylene glycol and its esters, sodium laurylsulfate, ammonium laurylsulfate, laurylsulfate amines, alkyl-substituted aromatic sulfonic acid salts, alkylphosphoric acid salts, aliphatic or aromatic sulfonic acid-formalin condensates, laurylamidopropylbetaine, laurylaminoacetylbetaine, polyethylene glycol fatty acid esters, polyoxyethylene-alkylamines, perfluoroalkylsulfonic acid salts, perfluoroalkylcarboxylic acid salts, perfluoroalkyl-ethyleneoxide adducts, perfluoroalkyltrimethylammonium salts, perfluoroalkyl group and hydrophilic group-containing oligomers, perfluoroalkyl group and oleophilic group-containing oligomers, perfluoroalkyl group-containing urethanes. The amount of the surfactant to be in the liquid-crystal composition varies depending on the type of the surfactant and the compositional ratio of the composition. Generally, it may be from 100 ppm to 5%, preferably from 0.1 to 1% by weight of the liquid-crystal composition.

An ordinary photocationic polymerization initiator is added to the compositions (MIX1) to (MIX8) of the invention. The photocationic polymerization initiator includes, for example, diaryliodonium salts (hereinafter abbreviated to DAS), triarylsulfonium salts (hereinafter abbreviated to TAS). DAS includes diphenyliodonium tetrafluoroborate, diphenyliodonium hexafluorophosphate, diphenyliodinium hexafluoroarsenate, diphenyliodonium trifluoromethanesulfonate, diphenyliodoniumtrifluoroacetate, diphenyliodinium p-toluenesulfonate, diphenyliodonium tetra(pentafluorophenyl)borate, 4-methoxyphenylphenyliodonium tetrafluoroborate, 4-methoxyphenylphenyliodonium hexafluorophosphonate, 4-methoxyphenylphenyliodonium hexafluoroarsenate, 4-methoxyphenylphenyliodonium trifluoromethanesulfonate, 4-methoxyphenylphenyliodonium trifluoroacetate, 4-methoxyphenylphenyliodonium p-toluenesulfonate, 4-methoxyphenylphenyliodonium diphenyliodonium tetra(pentafluorophenyl)borate, bis(4-tert-butylphenyl)iodonium diphenyliodonium tetrafluoroborate, bis(4-tert-butylphenyl)iodonium diphenyliodonium hexafluoroarsenate, bis(4-tert-butylphenyl)iodonium diphenyliodonium trifluoromethanesulfonate, bis(4-tert-butylphenyl)iodonium trifluoroacetate, bis(4-tert-butylphenyl)iodonium p-toluenesulfonate, and bis(4-tert-butylphenyl) iodonium diphenyliodonium tetra(pentafluorophenyl)borate.

A photosensitizer such as thioxanthone, phenothiazine, chlorothioxanthone, xanthone, anthracene, diphenylanthracene or rubrene may be added to DAS for further increasing the sensitivity of the initiator.

TAS includes triphenylsulfonium tetrafluoroborate, triphenylsulfonium hexafluorophosphate, triphenylsulfonium hexafluoroarsenate, triphenylsulfonium trifluoromethanesulfonate, triphenylsulfonium trifluoroacetate, triphenylsulfonium p-toluenesulfonate, triphenylsulfonium tetra(pentafluorophenyl)borate, 4-methoxyphenyldiphenylsulfonium tetrafluoroborate, 4-methoxyphenyldiphenylsulfonium hexafluorophosphonate, 4-methoxyphenyldiphenylsulfonium hexafluoroarsenate, 4-methoxyphenyldiphenylsulfonium trifluoromethanesulfonate, 4-methoxyphenyldiphenylsulfonium trifluoroacetate, 4-methoxyphenyldiphenylsulfonium p-toluenesulfonate, 4-methoxyphenyldiphenylsulfonium triphenylsulfonium tetra(pentafluorophenyl)borate, 4-phenylthiophenyldiphenylsulfonium tetrafluoroborate, 4-phenylthiophenyldiphenylsulfonium hexafluorophosphonate, 4-phenylthiophenyldiphenylsulfonium hexafluoroarsenate, 4-phenylthiophenyldiphenylsulfonium trifluoromethanesulfonate, 4-phenylthiophenyldiphenylsulfonium p-toluenesulfonate, and 4-phenylthiophenyldiphenylsulfonium tetra(pentafluorophenyl)borate.

Concrete examples of trade names of the photocationic polymerization initiators are Midori Chemical's DTS-102; UCC's Silacure UVI-6990, Silacure UVI-6974, Silacure UVI-6992; Asahi Denka Kogyo's Adeka Optomer SP-150, SP-152, SP-170, SP-172; Rhodia's Photoinitiator 2074; Ciba Specialty Chemicals' Irgacure 250; GE Silicons' UV-9380C.

Preferably, the amount of the photocationic polymerization initiator is from 0.01 to 20% by weight, more preferably from 0.1 to 10% by weight, even more preferably from 1 to 10% by weight, relative to 100% by weight of the composition (MIX1) to (MIX8) of the invention.

The liquid-crystal film of the invention may be produced by applying the photopolymerizable composition of the invention onto a support to form a film thereon followed by exposing the film to light so as to fix the nematic orientation of the liquid-crystal composition in the film. The supporting substrate may be any one capable of forming thereon a film of the liquid-crystal composition, including, for example, triacetyl cellulose, polyvinyl alcohol, polyimide, polyester, polyarylate, polyetherimide, polyethylene terephthalate, polyethylene naphthalate. In addition, other commercial products such as JSR's Arton, Nippon Zeon's Zeonex and Zeonoa, Mitsui Chemical's Apel are also usable herein. The supports may be uniaxially stretched films or biaxially stretched films.

In producing the liquid-crystal orientation film of the invention, it is especially desirable that a triacetyl cellulose film is used for the supporting substrate. A triacetyl cellulose film may be used as the supporting substrate directly as it is, but if desired, the film may be subjected to surface treatment such as saponification treatment, corona discharge treatment or UV-ozone treatment.

For forming the film, the photopolymerizable liquid-crystal composition may be dissolved in a suitable solvent and the resulting solution may be applied to the substrate. The solvent may be benzene, toluene, xylene, mesitylene, n-butylbenzene, diethylbenzene, tetralin, methoxybenzene, chlorobenzene, 1,2-dimethoxybenzene, ethylene glycol dimethyl ether, diethylene glycol dimethyl ether, acetone, methyl ethyl ketone, methyl isobutyl ketone, cyclohexanone, ethyl acetate, ethyl lactate, methyl lactate, ethylene glycol monomethyl ether acetate, propylene glycol monomethyl ether acetate, propylene glycol monoethyl ether acetate, γ-butyrolactone, 2-pyrrolidone, N-methyl-2-pyrrolidone, dimethylformamide, chloroform, dichloromethane, carbon tetrachloride, dichloroethane, tetrachloroethylene, trichloroethylene, tetrachloroethylene, chlorobenzene, t-butyl alcohol, diacetone alcohol, glycerin, monoacetin, ethylene glycol, triethylene glycol, hexylene glycol, ethylene glycol monomethyl ether, ethyl cellosolve, butyl cellosolve, propylene glycol monomethyl ether acetate, propylene glycol monoethyl ether acetate, or a mixed solvent of two or more of these solvents.

For applying the photopolymerizable liquid-crystal composition onto a substrate, for example, employable is a film-forming method of spin coating, roll coating, curtain coating, flow coating, printing, microgravure coating, gravure coating, wire bar coating, dipping, spraying, meniscus coating or casting to form a thin film on a substrate, and the film may be dried to remove the solvent from it.

Preferred methods for surface orientation treatment of substrates include a method of forming a thin film of polyimide or polyvinyl alcohol and rubbing it with a rayon cloth; a method of depositing silicon oxide on the film in a mode of oblique vapor deposition; and a method of rubbing-free orientation of using a stretched film, a polarized UV-oriented film or ionic beams. In addition, metal substrates of aluminium, iron or copper of which the surface is grooved in slits; and glass substrates of alkali glass, borosilicate glass or flint glass etched in slits may also be used as oriented substrates.

The oriented liquid-crystal layer is irradiated with electromagnetic waves such as UV rays or electron rays, whereby the orientation is fixed. The UV rays preferably have a longer wavelength than 300 nm, not absorbed by the composition. The dose of the electron rays is preferably from 1 to 200 Mrad. This is because, if the dose is too large, then the copolymer may be degraded. The temperature for electromagnetic wave irradiation may be any one at which the composition is in a liquid-crystal condition. However, if it is higher than 100° C., then thermal polymerization may occur to disorder the orientation. Therefore, the temperature is preferably not higher than 100° C.

When an optical-active compound is added to the composition of the invention, then it exhibits a helical structure. Therefore, when the liquid-crystal compound in the composition is polymerized while oriented and in a liquid-crystal condition, then a retarder having a helical structure can be produced. When the helical pitch is 1/n of the wavelength of light (in which n indicates a mean refractive index of the optically-anisotropic thin film obtained), then the film may selectively reflect any of right-handed or left-handed circularly-polarized light having the wavelength depending on the direction of the helical structure of the film and according to a Bragg's rule. This means that the film is usable, for example, as a device having a circularly-polarized light separation function. The direction of the helical structure depends on the steric configuration of the optical-active compound. Suitably selecting the steric configuration of the optical-active compound to be in the composition makes it possible to induce a desired helical direction in the film formed.

For example, according to the method disclosed in JP-A 6-281814, a shaped article having a property of optical anisotropy is obtained in which the helical pitch continuously varies in the direction of the thickness of the shaped article, and the shaped article may reflect light that falls within a broad wavelength range in accordance with the pitch.

The thickness of the optically-anisotropic thin film having a fixed orientation varies depending on the desired optical function and other properties of the film and on the degree of optical anisotropy thereof. Accordingly, though not strictly defined, the preferred thickness of the film may fall between 0.05 and 50 μm, more preferably between 0.1 and 20 μm, even more preferably between 0.5 and 10 μm. Also preferably, the haze value of the optically-anisotropic thin film is at most 1.5%, more preferably at most 1.0%; the transmittance thereof is at least 80%, more preferably at least 85%. It is desirable that the transmittance of the film falls within the range as above in a visible light region. The haze value of at most 1.5% of the film is a preferred condition so as not cause a problem with the film in point of the polarizability thereof. The transmittance of at least 80% of the film is also a preferred condition so as to ensure the brightness of liquid-crystal display devices in which the optically-anisotropic thin film is used.

EXAMPLES

The invention is described in detail with reference to the following Examples. The phase transition temperature described in the Examples is determined as follows: A sample is put on a hot plate of a melting point analyzer fitted with a polarizing microscope, and heated at a rate of 1° C./min. C means a crystal; N means a nematic phase; SmA means a smectic A phase; SmC means a smectic C phase; and I means an isotropic liquid. NI point means the uppermost limit temperature of a nematic phase, and this is a transition temperature from N to I. "C 50 N 63 I" is meant to indicate transition from C to N at 50° C. and transition from N to I at 63° C.

The pencil hardness is determined according to a method in JIS, "JIS-K-5400, 8.4 Pencil Scratch Test". The Cellotape (adhesive tape) peeling test is a test method in JIS, "JIS-5400, 8.5 Adhesiveness (8.5.2 Cross-Cut Tape Method)". Briefly, the adhesiveness of a sample is determined according to the number of remaining crosscuts of the total 100 crosscuts. The substrate used in the test is a saponified TAC film (hereinafter this is referred to as "saponified TAC").

The orientation condition of the liquid-crystal molecules on a substrate is confirmed as follows: The film sample to be analyzed is sandwiched between two polarizers set in a cross-Nicol in such a manner that the angle between the rubbing direction and the absorption axis of the polarizing element of the cross-Nicol could be 45 degrees. On a backlight, the intensity of the transmitted light through the set is read. From the angle dependency of the thus-read transmitted light intensity, the orientation condition of the sample is determined. While the sample set is inclined in the rubbing direction, the light transmission through the set is observed. When an asymmetric change on the right and left sides at the center of the front side is confirmed, then this means that the orientation vector of the liquid-crystal skeleton is inclined to the TAC substrate. Therefore, it is judged that this case is in hybrid orientation. When the light transmission through the sample set is observed while the set is inclined in the rubbing direction and when a symmetric change on the right and left sides at the center of the front side is confirmed, then this means that the orientation vector of the liquid-crystal skeleton is parallel to the TAC substrate. Therefore, it is judged that this case is in homogeneous orientation.

The heat resistance test is carried out as follows: A polyamic acid (Chisso's PIA5310) is applied onto a glass substrate, and heated at 210° C. for 30 minutes. This is used as a supporting substrate. The surface of the polyimide formed by the heating is rubbed with a rayon cloth, and a composition to be tested is applied onto it by the use of a bar coater. Thus coated, the sample is put on a hot plate heated at 70° C. for 3 minutes for the purpose of removing the solvent, and then cooled, whereby the coating composition is oriented. The resulting film is exposed to UV rays of 30 mW/cm$^2$ (365 nm) from an ultra-high-pressure mercury lamp (250 W), at 25° C. for 30 seconds, and the composition is thereby polymerized to form a liquid-crystal oriented film for heat resistance test. The retardation of the thus-formed film is determined at 25° C. for a wavelength of 550 nm. Then, the film is put in an oven at 100° C. for 500 hours, and its retardation is again determined at 25° C. The retardation change before and after the heating test is confirmed. In the following description, a volume unit, liter is expressed by a symbol L. The compositional ratio of the elution solvent in chromatography as well as that of the mixed solvent mentioned below is by volume.

Example 1

First Stage:

Production of ethyl 4-[6-(3-methyloxetan-3-ylmethoxy)hexyloxy]benzoate:

A reaction mixture comprising 84 g of 3-[(6-bromohexyloxy)methyl]-3-methyloxetane, 50 g of ethyl 4-hydroxybenzoate, 50 g of potassium carbonate and 600 ml of dimethylformamide was stirred at 90° C. for 4 hours. Water was added to the reaction mixture and the reaction was stopped. This was extracted with ethyl acetate, and the organic layer was washed with aqueous 2 N-sodium hydroxide solution and water in that order, and then dried with anhydrous magnesium sulfate. The solvent was evaporated away, and the resulting residue was purified through silica gel chromatography (elution solvent:toluene/ethyl acetate=8/2), and 85 g of ethyl 4-[6-(3-methyloxetan-3-ylmethoxy)hexyloxy]benzoate was obtained.

Second Stage:

Production of 4-[6-(3-methyloxetan-3-ylmethoxy)hexyloxy]benzoic Acid:

A reaction mixture comprising 83 g of ethyl 4-[6-(3-methyloxetan-3-ylmethoxy)hexyloxy]benzoate, 12 g of sodium hydroxide, 50 ml of water and 200 ml of Solmix (registered trade mark) was refluxed for 2 hours. This was made acidic with hydrochloric acid, and extracted with ethyl acetate. The organic layer was dried with anhydrous magnesium sulfate. The solvent was evaporated away, and 63 g of 4-[6-(3-methyloxetan-3-ylmethoxy)hexyloxy]benzoic acid (OX1) was obtained. m.p.: 58.5° C.

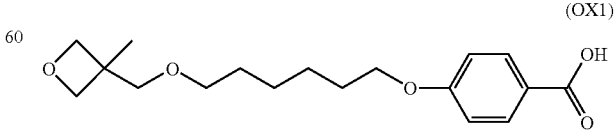

(OX1)

In the same manner as above, the following compounds were produced.

4-[6-(3-ethyloxetan-3-ylmethoxy)hexyloxy]benzoic acid (OX2) (m.p. : 61° C.)

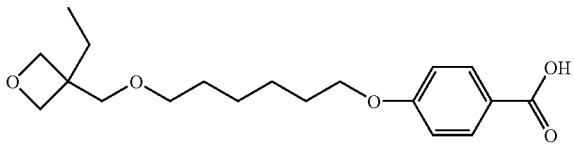
(OX2)

4-[4-(3-ethyloxetan-3-ylmethoxy)butyloxy]benzoic acid (OX3)
(m.p.: 75.3-77.7° C.)

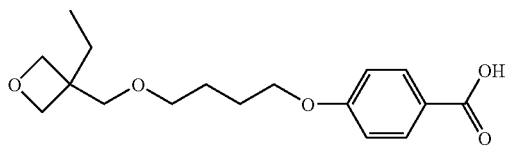
(OX3)

2-fluoro-4-[4-(3-ethyloxetan-3-ylmethoxy)butyloxy]benzoic acid (OX4) (m.p. : 75-80° C.)

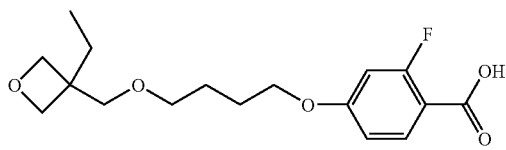
(OX4)

Production of 4-(3-methyloxetan-3-ylmethoxy)benzoic Acid:

First Stage:

116 g of 3-ethyl-3-hydroxymethyloxetane (Toa Gosei's trade name, OXT-101) was added to 500 ml of pyridine, and cooled to 0° C. with stirring. 190 g of p-toluenesulfonyl chloride divided into a few portions was added to it intermittently. Kept at 0° C., this was stirred for 5 hours, and then 1 L of ice-water was poured into the reaction mixture. This was extracted with 500 ml of diethyl ether. The diethyl ether layer was washed with 3% hydrochloric acid until its pH became acidic, and then washed with saturated sodium carbonate solution and water in this order, and thereafter dried with anhydrous magnesium sulfate. The solvent was evaporated away, and 243 g of 3-[(tosyloxy)methyl]-3-ethyloxetane was obtained.

Second Stage:

50 g of ethyl hydroxybenzoate and 21 g of potassium hydroxide were added to 400 ml of dimethylformamide, and stirred at 70° C. for 1 hour. This was cooled to 45° C., and 100 g of 3-[(tosyloxy)methyl]-3-ethyloxetane was dropwise added to it. Kept at 45° C., this was stirred for 3 hours. Water and toluene were added to it for liquid-liquid separation. The toluene layer was washed with 3% hydrochloric acid, saturated sodium hydrogencarbonate and water, and then toluene was evaporated away. To the resulting residue, added were 50 g of sodium hydroxide, 500 ml of ethanol and 200 ml of water, and this was refluxed for 2 hours. Ethanol was evaporated away, and the resulting residue was poured into 500 ml of 5% hydrochloric acid, and a crystal was thus formed. The crystal taken out through filtration was recrystallized from a mixed solvent of ethanol and water, and 60 g of 4-(3-ethyloxetan-3-ylmethoxy)benzoic acid (OX5) was obtained. Its melting point was 127.5° C.

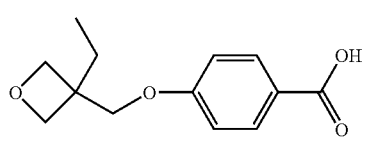
(OX5)

19 g of ethyl hydroxycinnamate and 7.3 g of potassium hydroxide were added to 150 ml of ethanol, and stirred at 50° C. for 1 hour. This was cooled to 40° C., and 35 g of 3-[(tosyloxy)methyl]-3-ethyloxetane was dropwise added to it. Then, this was refluxed for 3 hours. Ethanol was evaporated away, and water and toluene were added to it for liquid-liquid separation. The toluene layer was washed with 3% hydrochloric acid, saturated sodium hydrogencarbonate and water, and then toluene was evaporated away. To the resulting residue, added were 20 g of sodium hydroxide, 100 ml of ethanol and 50 ml of water, and this was refluxed for 2 hours. Ethanol was evaporated away, and the resulting residue was poured into 500 ml of 5% hydrochloric acid, and a crystal was thus formed. The crystal taken out through filtration was recrystallized from a mixed solvent of ethanol and water, and 5 g of 4-(3-ethyloxetan-3-ylmethoxy)cinnamic acid (OX6) was obtained. Its melting point was 127.5° C.

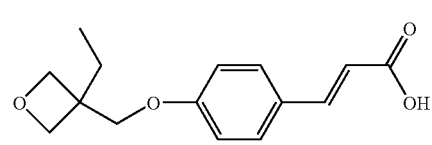
(OX6)

17.4 g of ethyl 3-(4-hydroxyphenyl)propionate and 6.1 g of potassium hydroxide were added to 150 ml of ethanol, and stirred at 60° C. for 1 hour. This was cooled to 40° C., and 30 g of 3-[(tosyloxy)methyl]-3-ethyloxetane was dropwise added to it. Then, this was refluxed for 3 hours. Ethanol was evaporated away, and water and toluene were added to it for liquid-liquid separation. The toluene layer was washed with 3% hydrochloric acid, saturated sodium hydrogencarbonate and water, and then toluene was evaporated away. To the resulting residue, added were 20 g of sodium hydroxide, 100 ml of ethanol and 50 ml of water, and this was refluxed for 2 hours. Ethanol was evaporated away, and the resulting residue was poured into 500 ml of 5% hydrochloric acid, and a crystal was thus formed. The crystal taken out through filtration was recrystallized from a mixed solvent of ethanol and water, and 5 g of [4-(3-ethyloxetan-3-ylmethoxy)phenyl]propionic acid (OX7) was obtained. Its melting point was 85° C.

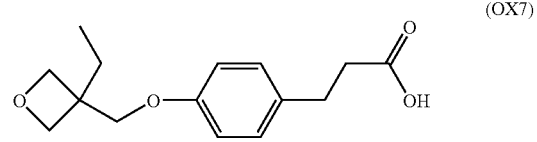
(OX7)

Third Stage:

6.9 g of 4-[6-(3-ethyloxetan-3-ylmethoxy)hexyloxy]benzoic acid and 4 g of 4-trifluoromethoxy-3-fluorophenol were dissolved in 150 ml of methylene chloride and cooled to 5° C., and 0.1 g of dimethylaminopyridine and 4.3 g of 1-ethyl-3-(3-dimethylaminopropyl)carbodiimide hydrochloride were added to it and stirred at room temperature for 12 hours. 200 ml of water was added to it for liquid-liquid separation, and the organic layer was dried with anhydrous magnesium sulfate. The solvent was evaporated away, and the resulting residue was purified through silica gel chromatography (elution solvent: toluene/ethyl acetate=9/1), and 7.4 g of a compound No. 61 was obtained.

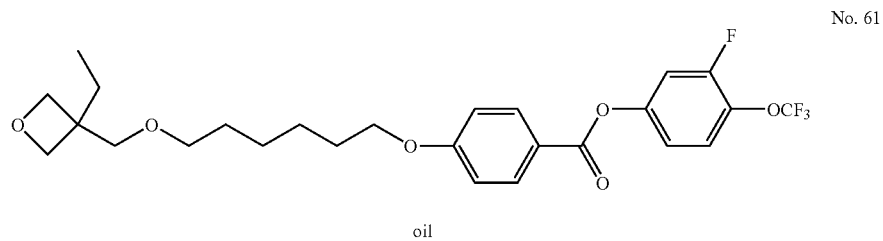

No. 61 oil

A compound No. 12 was produced through esterification of 4-[6-(3-methyloxetan-3-ylmethoxy)hexyloxy]benzoic acid (OX1) with 3-fluoro-4-trifluoromethoxyphenol. The esterification was attained according to the method of the third stage in Example 1. The structure and the property of the compound No. 12 are shown below.

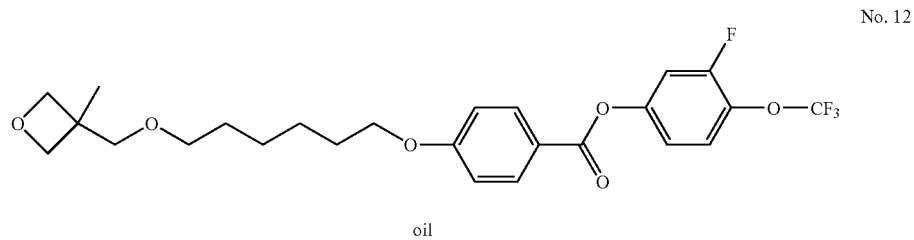

No. 12 oil

A compound No. 50 was produced through esterification of 4-(3-ethyloxetan-3-ylmethoxy)benzoic acid (OX5) with 4-trifluoromethoxyphenol. The esterification was attained according to the method of the third stage in Example 1. The structure and the melting point of the compound No. 50 are shown below.

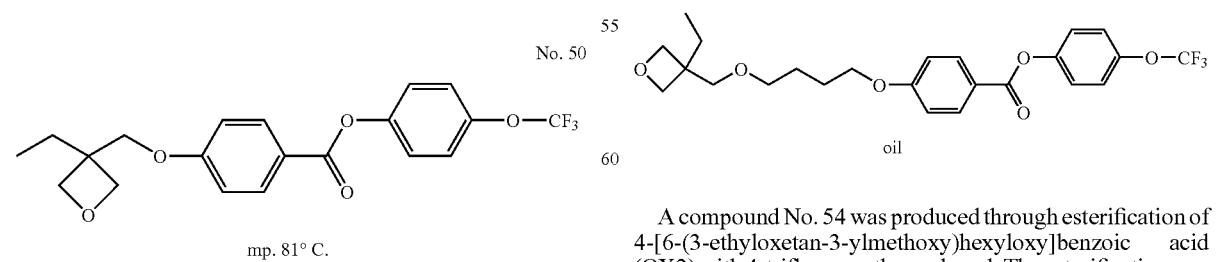

No. 50 mp. 81° C.

A compound No. 52 was produced through esterification of 4-[4-(3-ethyloxetan-3-ylmethoxy)butyloxy]benzoic acid (OX3) with 4-trifluoromethoxyphenol. The esterification was attained according to the method of the third stage in Example 1. The structure and the property of the compound No. 52 are shown below.

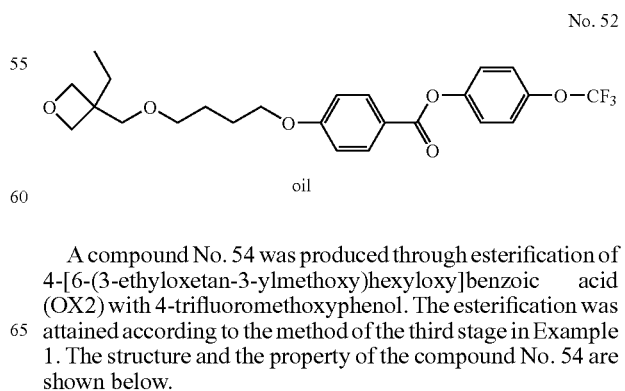

No. 52 oil

A compound No. 54 was produced through esterification of 4-[6-(3-ethyloxetan-3-ylmethoxy)hexyloxy]benzoic acid (OX2) with 4-trifluoromethoxyphenol. The esterification was attained according to the method of the third stage in Example 1. The structure and the property of the compound No. 54 are shown below.

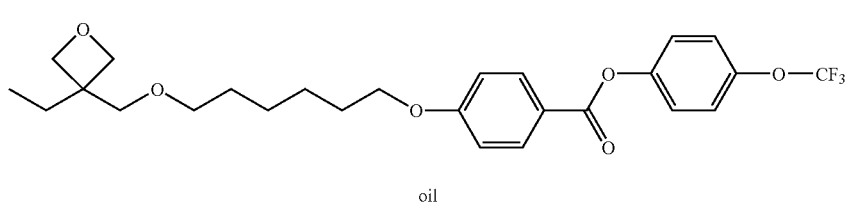

No. 54 oil

A compound No. 56 was produced through esterification of 4-(3-ethyloxetan-3-ylmethoxy)benzoic acid (OX5) with 3-fluoro-4-trifluoromethoxyphenol. The esterification was attained according to the method of the third stage in Example 1. The structure and the melting point of the compound No. 56 are shown below.

No. 56

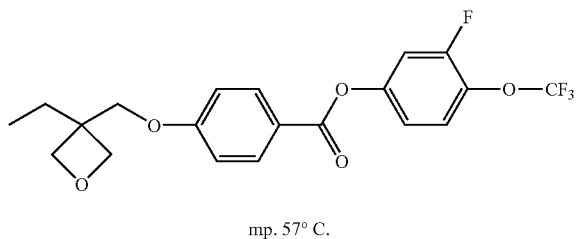

mp. 57° C.

5.3 g of 4-(3-ethyloxetan-3-ylmethoxy)cinnamic acid (OX6) and 4 g of 3-fluoro-4-trifluoromethoxyphenol were added to 100 ml of methylene chloride and cooled to 0° C. 4.5 g of dicyclohexylcarbodiimide and 0.01 g of dimethylaminopyridine were added to it and stirred for 12 hours. Water was added to the reaction mixture for liquid-liquid separation, and the organic layer was washed with 5% hydrochloric acid and aqueous saturated sodium carbonate solution, and dried with anhydrous magnesium sulfate. The solvent was evaporated away, and the resulting residue was purified through silica gel column chromatography (elution solvent: toluene/ethyl acetate=19/1) and recrystallization from ethanol to obtain a compound No. 118. The structure and the melting point of the compound No. 118 are shown below.

No. 118

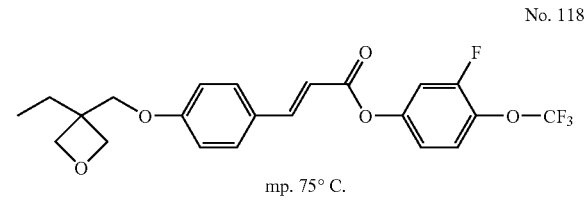

mp. 75° C.

A compound No. 123 was produced through esterification of [4-(3-ethyloxetan-3-ylmethoxy)phenyl]propionic acid (OX7) with 3-fluoro-4-trifluoromethoxyphenol. The esterification was attained according to the method of producing the compound No. 118. The structure, and the property or the phase transition temperature of the compound No. 123 are shown below.

No. 123

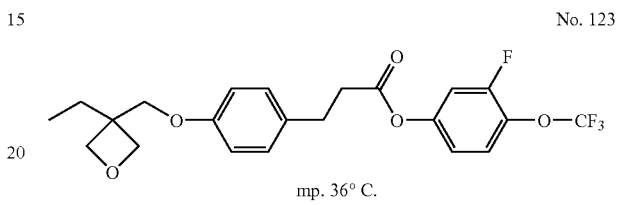

mp. 36° C.

Example 2

First Stage:

Production of 4-benzyloxy-4'-(trifluoromethoxy)biphenyl:

A reaction mixture comprising 6.7 g of 4-benzyloxybromobenzene, 5.0 g of 4-(trifluoromethoxy)benzeneboronic acid, 0.3 g of tetrakis(triphenylphosphine)palladium(0), 5.1 g of sodium carbonate, 100 ml of ethylene glycol dimethyl ether and 20 ml of pure water was refluxed for 5 hours. The reaction mixture was extracted with toluene, and the organic layer was dried with anhydrous magnesium sulfate. The solvent was evaporated away, and the resulting residue was purified through silica gel chromatography (elution solvent: heptane/toluene=7/3) and recrystallized from heptane, and 3.0 g of 4-benzyloxy-4'-(trifluoromethoxy)biphenyl was obtained. m.p.: 136-137.2° C.

Second Stage:

Production of 4-hydroxy-4'-(trifluoromethoxy)biphenyl:

A reaction mixture comprising 3.0 g of 4-benzyloxy-4'-(trifluoromethoxy)biphenyl, 0.1 g of palladium hydroxide and 30 ml of ethyl acetate was filled with hydrogen gas, and stirred at room temperature for 8 hours. The reaction mixture was filtered, and the solvent of the filtrate was evaporated away. The resulting residue was recrystallized from heptane, and 1.5 g of 4-hydroxy-4'-(trifluoromethoxy)biphenyl was obtained. m.p.: 140-140.5° C.

Third Stage:

1.85 g of 4-[6-(3-ethyloxetan-3-ylmethoxy)hexyloxy]benzoic acid (OX2) and 1.4 g of 4-hydroxy-4'-(trifluoromethoxy)biphenyl were dissolved in 50 ml of methylene chloride, and cooled to 5° C. 0.1 g of dimethylaminopyridine and 1.2 g of 1-ethyl-3-(3-dimethylaminopropyl)carbodiimide hydrochloride were added to it, and stirred at room temperature for 12 hours. 50 ml of water was added to it for liquid-liquid separation, and the organic layer was dried with anhydrous magnesium sulfate. The solvent was evaporated away, and the resulting residue was purified through silica gel chromatography (elution solvent: toluene/ethyl acetate=9/1), and recrystallized from heptane/ethyl acetate=1/1, and 1.8 g of a compound No. 77 was obtained.

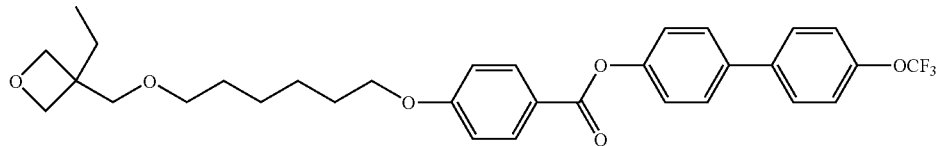

No. 77

C 84 SmC 103 SmA 134I

Example 3

A reaction mixture comprising 5.0 g of 4-[6-(3-ethyloxetan-3-ylmethoxy)hexyloxy]benzoic acid and 50 ml of thionyl chloride was refluxed for 2 hours. Thionyl chloride was evaporated away from the reaction mixture, and the resulting residue was dissolved in 50 ml of tetrahydrofuran. This was dropwise added to a solution of 2.7 g of 4-(trifluoromethoxy)aniline, 1.3 g of pyridine and 50 ml of tetrahydrofuran cooled at 5° C. This was stirred at room temperature for 2 hours, and then subjected to liquid-liquid separation with methylene chloride added thereto. The organic layer was dried with anhydrous magnesium sulfate. The solvent was evaporated away, and the resulting residue was purified through silica gel chromatography (elution solvent: toluene/ethyl acetate 95/5), and recrystallized from heptane/ethyl acetate=1/1, and 1.8 g of a compound No. 111 was obtained.

Example 4

Composition Example of (MIX4)

A composition (CL1) of 50% by weight of a compound No. 12 and 50% by weight of a bifunctional oxetane (K1) was prepared. The composition exhibited a nematic liquid-crystal phase at room temperature, and its NI point was 108° C. Not undergoing phase separation, the compound No. 12 showed good compatibility. The composition (CL1) did not immediately crystallize even at room temperature, but kept a liquid-crystal condition. When the composition (CL1) was applied

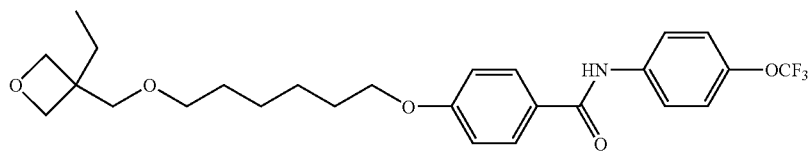

No. 111

C 144 I onto a rubbed, saponified TAC film, and oriented thereon, then it showed hybrid orientation.

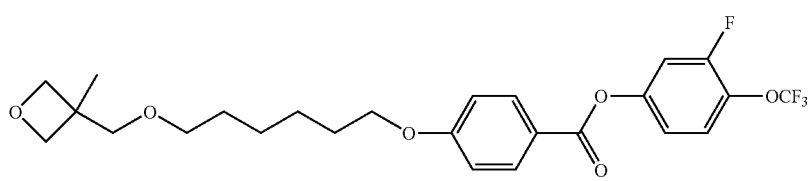

No. 12

50 wt. %

-continued (K1)

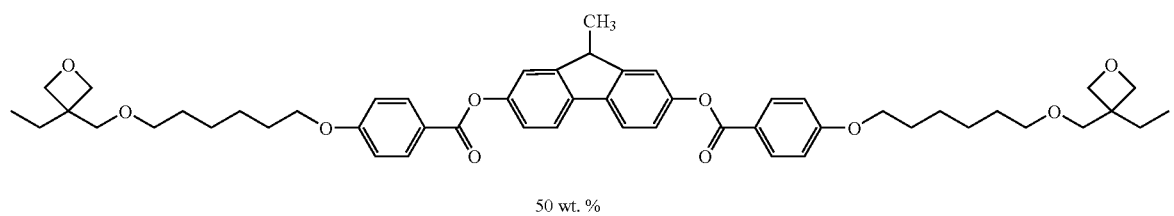

50 wt. %

Example 5

Composition Example i of (MIX2)

A composition (CL2) of 30% by weight of a compound No. 54 and 70% by weight of a bifunctional oxirane (K2) was prepared. The composition exhibited a nematic liquid-crystal phase at room temperature, and its NI point was 95° C. Not undergoing phase separation, the compound No. 54 showed good compatibility. The composition (CL2) did not immediately crystallize even at room temperature, but kept a liquid-crystal condition. When the composition (CL2) was applied onto a rubbed, saponified TAC film, and oriented thereon, then it showed hybrid orientation.

Example 6

Composition Example ii of (MIX2)

A composition (CL3) of 30% by weight of a compound No. 12 and 70% by weight of a bifunctional oxirane (K3) was prepared. The composition exhibited a nematic liquid-crystal phase at room temperature, and its NI point was 141° C. Not undergoing phase separation, the compound No. 12 showed good compatibility. The composition (CL3) did not immediately crystallize even at room temperature, but kept a liquid-crystal condition. When the composition (CL3) was applied onto a rubbed, saponified TAC film, and oriented thereon, then it showed hybrid orientation.

No. 54

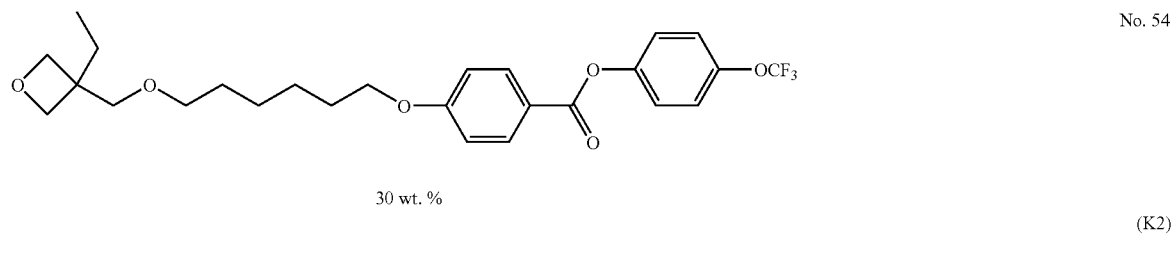

30 wt. %

(K2)

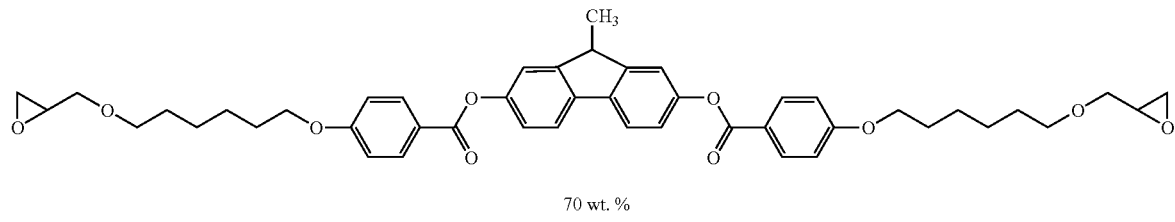

70 wt. %

No. 12

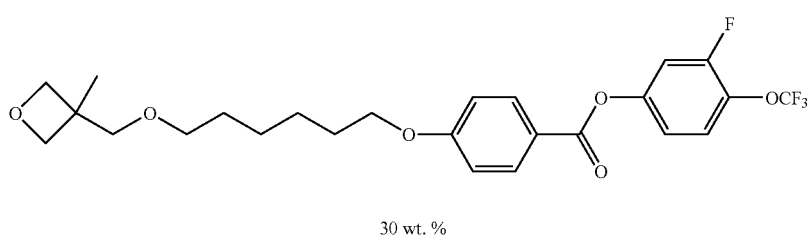

30 wt. %

-continued (K3)

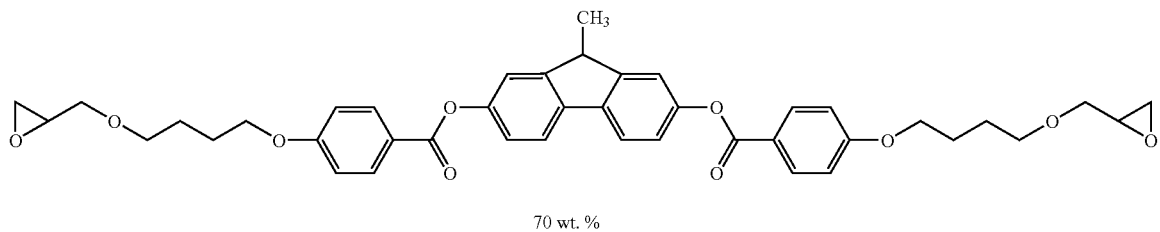

70 wt. %

Example 7

Composition Example iii of (MIX2)

A composition (CL4) of 35% by weight of a compound No. 56 and 65% by weight of a bifunctional oxirane (K3) was prepared. The composition exhibited a nematic liquid-crystal phase at room temperature, and its NI point was 131° C. Not undergoing phase separation, the compound No. 56 showed good compatibility. The composition (CL4) did not immediately crystallize even at room temperature, but kept a liquid-crystal condition. When the composition (CL4) was applied onto a rubbed, saponified TAC film, and oriented thereon, then it showed hybrid orientation.

Example 8

Composition Example iv of (MIX2)

A composition (CL5) of 40% by weight of a compound No. 118 and 60% by weight of a bifunctional oxirane (K3) was prepared. The composition exhibited a nematic liquid-crystal phase at room temperature, and its NI point was 129° C. Not undergoing phase separation, the compound No. 118 showed good compatibility. The composition (CL5) did not immediately crystallize even at room temperature, but kept a liquid-crystal condition. When the composition (CL5) was applied No. 56

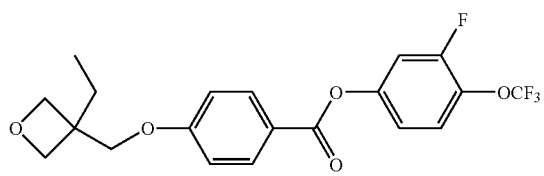

35 wt. %

(K3)

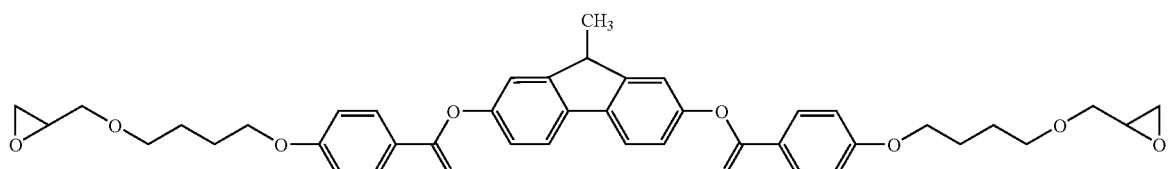

65 wt. % onto a rubbed, saponified TAC film, and oriented thereon, then it showed hybrid orientation.

No. 118

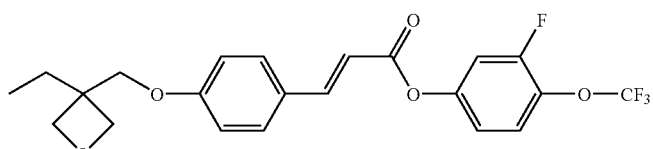

40 wt. %

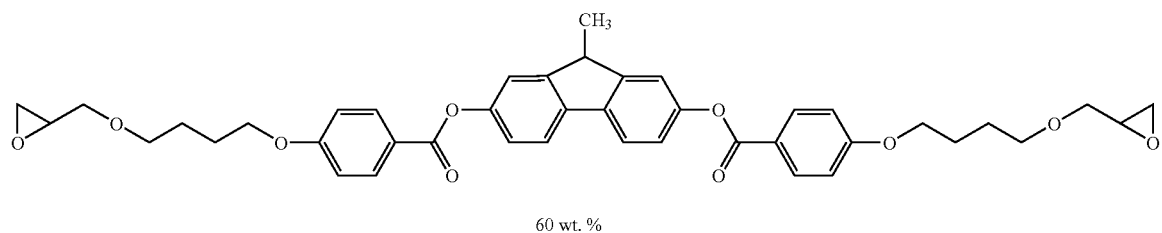

(K3)

60 wt. %

Example 9

Composition Example v of (MIX2)

A composition (CL6) of 30% by weight of a compound No. 123 and 70% by weight of a bifunctional oxirane (K3) was prepared. The composition exhibited a nematic liquid-crystal phase at room temperature, and its NI point was 118° C. Not undergoing phase separation, the compound No. 123 showed good compatibility. The composition (CL6) did not immediately crystallize even at room temperature, but kept a liquid-crystal condition. When the composition (CL6) was applied onto a rubbed, saponified TAC film, and oriented thereon, then it showed hybrid orientation.

Example 10

Composition Example of (MIX3)

A composition (CL7) comprising 30% by weight of a compound No. 77, 20% by weight of a monofunctional oxetane (K4) and 50% by weight of a bifunctional oxirane (K3) was prepared. The composition exhibited a nematic liquid-crystal phase at room temperature, and its NI point was 127° C. Not undergoing phase separation, the compound No. 77 showed good compatibility. The composition (CL7) did not immediately crystallize even at room temperature, but kept a liquid-crystal condition. When the composition (CL7) was

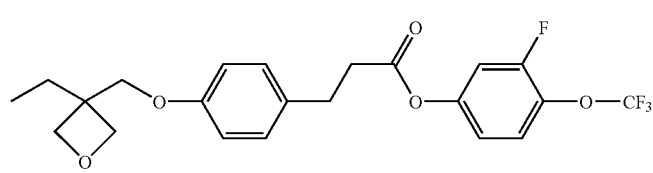

No. 123

30 wt. %

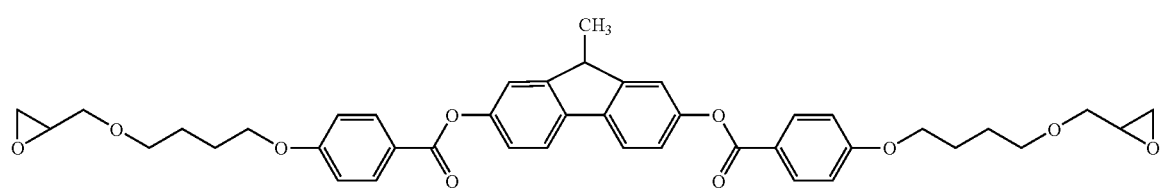

(K3)

70 wt. % applied onto a rubbed, saponified TAC film, and oriented thereon, then it showed hybrid orientation.

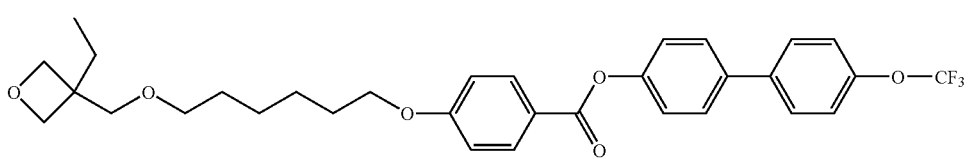

No. 77

30 wt. %

-continued

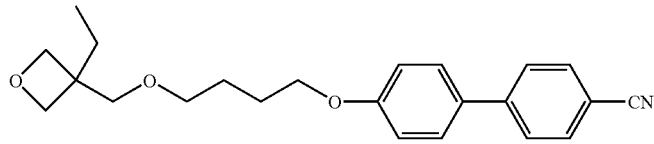

20 wt. %

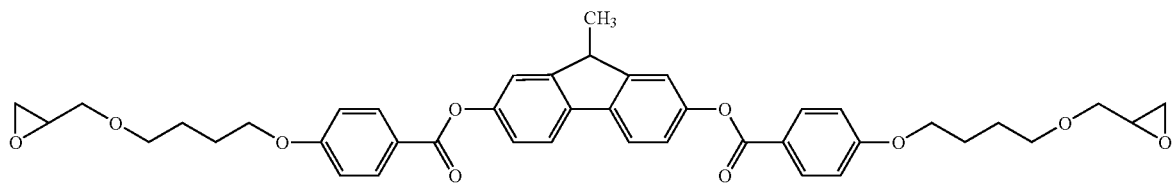

50 wt. %

Example 11

Production 1 of Oriented Film through Irradiation with UV Rays

A solution prepared by dissolving 100% by weight of the composition (CL1) and 3% by weight of DTS-102 (by Midori Chemical) in 300% by weight of a mixed solvent (toluene/cyclopentanone=2/1) was applied onto a saponified TAC that had been rubbed with a rayon cloth on its surface, using a bar coater. After thus coated, this was heated in an oven at 60° C. for 5 minutes, whereby the solvent was removed and the composition (CL1) was thus oriented. Kept at the same temperature, this was exposed to UV rays of 30 mW/cm$^2$ (365 nm) from an ultra-high-pressure mercury lamp (250 W), at 25° C. for 30 seconds.

The composition (CL1) polymerized while it kept its orientation condition (hybrid orientation), and its surface hardness was 2H as pencil hardness. After a heat resistance test at 100° C. for 500 hours, this showed no retardation change. Thus, a liquid-crystal oriented film (F1) of good heat resistance was obtained.

Example 12

Production 2 of Oriented Film through Irradiation with UV Rays

A solution prepared by dissolving 100% by weight of the composition (CL2) and 3% by weight of DTS-102 in 300% by weight of a mixed solvent (toluene/cyclopentanone=2/1) was applied onto a saponified TAC that had been rubbed with a rayon cloth on its surface, using a bar coater. After thus coated, this was heated in an oven at 60° C. for 5 minutes, whereby the solvent was removed and the composition (CL2) was thus oriented. Kept at the same temperature, this was exposed to UV rays of 30 mW/cm$^2$ (365 nm) from an ultra-high-pressure mercury lamp (250 W), at 25° C. for 30 seconds. After the irradiation, the composition (CL2) polymerized while it kept its orientation condition (hybrid orientation), and its surface hardness was 2H as pencil hardness. After a heat resistance test at 100° C. for 500 hours, this showed no retardation change. Thus, a liquid-crystal oriented film (F2) of good heat resistance was obtained.

Example 13

Production 3 of Oriented Film through Irradiation with UV Rays

A solution prepared by dissolving 100% by weight of the composition (CL3) and 3% by weight of DTS-102 in 300% by weight of a mixed solvent (toluene/cyclopentanone=2/1) was applied onto a saponified TAC that had been rubbed with a rayon cloth on its surface, using a bar coater. After thus coated, this was heated in an oven at 70° C. for 5 minutes, whereby the solvent was removed and the composition (CL3) was thus oriented. Kept at the same temperature, this was exposed to UV rays of 30 mW/cm$^2$ (365 nm) from an ultra-high-pressure mercury lamp (250 W), at 25° C. for 30 seconds. After the irradiation, the composition (CL3) polymerized while it kept its orientation condition (hybrid orientation), and its surface hardness was 2H as pencil hardness. After a heat resistance test at 100° C. for 500 hours, this showed no retardation change. Thus, a liquid-crystal oriented film (F3) of good heat resistance was obtained.

Example 14

Production 4 of Oriented Film through Irradiation with UV Rays

A solution prepared by dissolving 100% by weight of the composition (CL4) and 3% by weight of DTS-102 in 300% by weight of a mixed solvent (toluene/cyclopentanone=2/1) was applied onto a saponified TAC that had been rubbed with a rayon cloth on its surface, using a bar coater. After thus coated, this was heated in an oven at 70° C. for 5 minutes, whereby the solvent was removed and the composition (CL4) was thus oriented. Kept at the same temperature, this was exposed to UV rays of 30 mW/cm$^2$ (365 nm) from an ultra-high-pressure mercury lamp (250 W), at 25° C. for 30 seconds. After the irradiation, the composition (CL4) polymerized while it kept its orientation condition (hybrid orientation), and its surface hardness was 2H as pencil hardness. After a heat resistance test at 100° C. for 500 hours, this showed no retardation change. Thus, a liquid-crystal oriented film (F4) of good heat resistance was obtained.

Example 15

Production 5 of Oriented Film through Irradiation with UV Rays

A solution prepared by dissolving 100% by weight of the composition (CL5) and 3% by weight of DTS-102 in 300% by weight of a mixed solvent (toluene/cyclopentanone=2/1) was applied onto a saponified TAC that had been rubbed with a rayon cloth on its surface, using a bar coater. After thus coated, this was heated in an oven at 70° C. for 5 minutes, whereby the solvent was removed and the composition (CL5) was thus oriented. Kept at the same temperature, this was exposed to UV rays of 30 mW/cm² (365 nm) from an ultra-high-pressure mercury lamp (250 W), at 25° C. for 30 seconds. After the irradiation, the composition (CL5) polymerized while it kept its orientation condition (hybrid orientation), and its surface hardness was 2H as pencil hardness. After a heat resistance test at 100° C. for 500 hours, this showed no retardation change. Thus, a liquid-crystal oriented film (F5) of good heat resistance was obtained.

Example 16

Production 6 of Oriented Film through Irradiation with UV Rays

A solution prepared by dissolving 100% by weight of the composition (CL6) and 3% by weight of DTS-102 in 300% by weight of a mixed solvent (toluene/cyclopentanone=2/1) was applied onto a saponified TAC that had been rubbed with a rayon cloth on its surface, using a bar coater. After thus coated, this was heated in an oven at 70° C. for 5 minutes, whereby the solvent was removed and the composition (CL6) was thus oriented. Kept at the same temperature, this was exposed to UV rays of 30 mW/cm² (365 nm) from an ultra-high-pressure mercury lamp (250 W), at 25° C. for 30 seconds. After the irradiation, the composition (CL6) polymerized while it kept its orientation condition (hybrid orientation), and its surface hardness was 2H as pencil hardness. After a heat resistance test at 100° C. for 500 hours, this showed no retardation change. Thus, a liquid-crystal oriented film (F6) of good heat resistance was obtained.

Example 17

Production 7 of Oriented Film through Irradiation with UV Rays

A solution prepared by dissolving 100% by weight of the composition (CL7) and 3% by weight of DTS-102 in 300% by weight of a mixed solvent (toluene/cyclopentanone=2/1) was applied onto a saponified TAC that had been rubbed with a rayon cloth on its surface, using a bar coater. After thus coated, this was heated in an oven at 85° C. for 5 minutes, whereby the solvent was removed and the composition (CL7) was thus oriented. Kept at the same temperature, this was exposed to UV rays of 30 mW/cm² (365 nm) from an ultra-high-pressure mercury lamp (250 W), at 25° C. for 30 seconds. After the irradiation, the composition (CL7) polymerized while it kept its orientation condition (hybrid orientation), and its surface hardness was 2H as pencil hardness. After a heat resistance test at 100° C. for 500 hours, this showed no retardation change. Thus, a liquid-crystal oriented film (F7) of good heat resistance was obtained.

Comparative Example 1

A solution prepared by dissolving 100% by weight of a bifunctional acrylate compound (AC1) and 3% by weight of Irgacure 907 in 300% by weight of a mixed solvent (toluene/cyclopentanone=2/1) was applied onto a saponified TAC that had been rubbed with a rayon cloth on its surface, using a bar coater. After thus coated, this was heated in an oven at 85° C. for 5 minutes, whereby the solvent was removed and the compound (AC1) was thus oriented. Kept at the same temperature, this was exposed to UV rays of 30 mw/cm² (365 nm) from an ultra-high-pressure mercury lamp (250 W), in a nitrogen atmosphere at 25° C. for 30 seconds. After the irradiation, the compound (AC1) polymerized, and a liquid-crystal oriented film (FK1) showing homogeneous orientation was obtained.

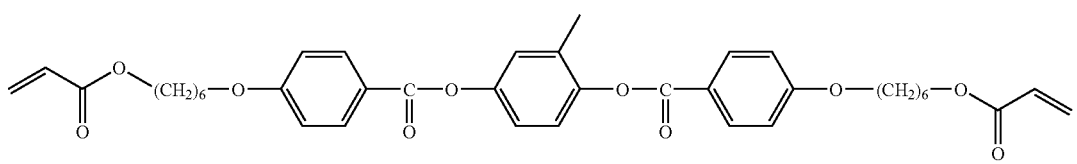

(AC1)

The liquid-crystal films thus obtained herein were tested according to a Cellotape (adhesive tape) peeling test and a pencil hardness test, and the test results are shown below.

| Film No. | Cellotape Peeling | Pencil Hardness | Orientation |
| --- | --- | --- | --- |
| F1 | 100/100 | 2H | hybrid |
| F2 | 100/100 | 2H | hybrid |
| F3 | 100/100 | 2H | hybrid |
| F4 | 100/100 | 2H | hybrid |
| F5 | 100/100 | 2H | hybrid |
| F6 | 100/100 | 2H | hybrid |
| F7 | 100/100 | 2H | hybrid |
| FK1 (Comparative Example 1) | 0/100 | H | homogeneous |

Cellotape Peeling Test:

In the Cellotape peeling test of the oriented film (FK1) that had been obtained through polymerization of a bifunctional acrylate in Comparative Example 1, all crosscuts peeled off, and no crosscut remained. Contrary to this, the oriented films obtained through polymerization of the composition of the invention kept all the crosscuts as such, and no crosscut peeled off.

Pencil Hardness Test:

The pencil hardness of the oriented film (FK1) was H; but the oriented films (F1), (F2), (F3), (F4), (F5), (F6) and (F7)

formed of the compositions (CL1), (CL2), (CL3), (CL4), (CL5), (CL6) and (CL7), respectively, all had a pencil hardness of 2H.

Heat Resistance Test:

Before and after the heat resistance test at 100° C. for 500 hours, the retardation change in the oriented films (F1), (F2), (F3), (F4), (F5), (F6) and (F7) was within 3%. This confirms good heat resistance of the films.

Orientation:

The composition that contains the compound of the invention showed nematic hybrid orientation on a rubbed saponified TAC film, even though any non-polymerizable compound such as surfactant is not added thereto (Example 4, Example 5, Example 6, Example 7, Example 8, Example 9 and Example 10). The film formed of a polymer produced through photopolymerization of the compound in the composition also kept hybrid orientation (Example 11, Example 12, Example 13, Example 14, Example 15, Example 16 and Example 17).

INDUSTRIAL APPLICABILITY

The composition and the polymer of the invention are usable for retarders, polarizing elements, liquid-crystal oriented films, antireflection films, selective reflection films and viewing angle compensatory films that are constitutive elements of liquid-crystal display devices. The compound of the invention is usable also for resins of high thermal conductivity, adhesives, synthetic polymers of mechanical anisotropy, cosmetics, decorations, non-linear optical materials and information memory materials.

What is claimed is:

1. A compound of a formula (1):

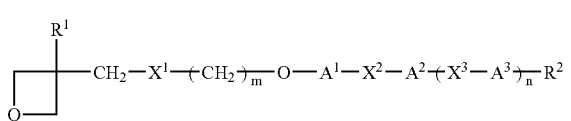

(1)

wherein $R^1$ represents a hydrogen atom or an alkyl group having from 1 to 5 carbon atoms; $R^2$ represents a hydrogen atom, —NCO, —NCS, —OCHF$_2$, —CH$_2$F, —OCF$_2$CF$_2$H, —OCF$_2$CHFCF$_3$, or —Y$^1$—(CF$_2$)s-CF$_3$, in which Y$^1$ represents —O—, —S—, —COO—, —OCO—, —CO—, —CH=CH—, or —C≡C—, s indicates an integer of from 0 to 10; $A^1$ represents a 1,4-phenylene group, or a 1,4-phenylene group in which any hydrogen atom is substituted with a halogen atom, a cyano group, a methyl group, an ethyl group, a methoxy group, a hydroxy group, a formyl group, an acetoxy group, an acetyl group, a carbonylmethyl group, a carbonyltrifluoromethyl group, a difluoromethyl group, or a trifluoromethyl group; $A^2$ and $A^3$ each independently represent a 1,4-cyclohexylene group, a 1,4-phenylene group, a pyridine-2,5-diyl group, a pyridazine-3,6-diyl group, a pyrimidine-2,5-diyl group, a naphthalene-2,6-diyl group, a tetrahydronaphthalene-2,6-diyl group, a 1,4-cyclohexylene group in which any hydrogen atom is substituted with a fluorine atom, or a 1,4-phenylene group in which any hydrogen atom is substituted with a halogen atom, a cyano group, a methyl group, an ethyl group, a methoxy group, a hydroxy group, a formyl group, an acetoxy group, an acetyl group, a carbonylmethyl group, a carbonyltrifluoromethyl group, a difluoromethyl group or a trifluoromethyl group; $X^1$ represents a single bond, —O— or —OCO—; $X^2$ and $X^3$ each independently represent a single bond, —CH=CH—COO—, —OOC—CH=CH—, —CH$_2$CH$_2$—COO—, —OOC—CH$_2$CH$_2$—, —COO—, —OCO—, —OCH$_2$—, —CH$_2$O—, —OCF$_2$—, —CF$_2$O—, —CH$_2$CH$_2$—, —C≡C—, —NHCO—, or —CONH—; m indicates an integer of from 0 to 20; and n indicates 1 or 0.

2. The compound as claimed in claim 1, wherein, in formula (1), $R^1$ is a methyl or ethyl group; $R^2$ is —Y$^1$—(CF$_2$)s—CF$_3$, in which Y$^1$ is —O—, —S—, —COO—, —OCO—, —CO—, —CH=CH—, or —C≡C—, s is an integer of from 0 to 10.

3. The compound as claimed in claim 1, wherein, in formula (1), $R^1$ is a methyl or ethyl group; $R^2$ is —Y$^1$—(CF$_2$)s—CF$_3$, in which Y$^1$ is —O—, s is an integer of from 0 to 10; $A^1$ is a 1,4-phenylene group, or a 1,4-phenylene group in which any hydrogen atom is substituted with a halogen atom, a methyl group, an acetyl group or a trifluoromethyl group; $A^2$ and $A^3$ are independently a 1,4-cyclohexylene group, a 1,4-phenylene group, a pyridine-2,5-diyl group, a pyridazine-3,6-diyl group, a pyrimidine-2,5-diyl group, a naphthalene-2,6-diyl group, a tetrahydronaphthalene-2,6-diyl group, or a 1,4-phenylene group in which any hydrogen atom is substituted with a halogen atom, a methyl group, an acetyl group or a trifluoromethyl group; $X^1$ is a single bond or —O—; $X^2$ and $X^3$ are independently a single bond, —CH=CH—COO—, —CH$_2$CH$_2$—COO—, —COO—, —C≡C—, or —CONH—.

4. The compound as claimed in claim 1, wherein, in formula (1), $R^1$ is a methyl or ethyl group; $R^2$ is —OCF$_3$; $A^1$ is a 1,4-phenylene group, or a 1,4-phenylene group in which any hydrogen atom is substituted with a halogen atom, a methyl group, an acetyl group or a trifluoromethyl group; $A^2$ and $A^3$ are independently a 1,4-cyclohexylene group, a 1,4-phenylene group, a pyridine-2,5-diyl group, a pyridazine-3,6-diyl group, a pyrimidine-2,5-diyl group, a naphthalene-2,6-diyl group, a tetrahydronaphthalene-2,6-diyl group, or a 1,4-phenylene group in which any hydrogen atom is substituted with a halogen atom, a methyl group, an acetyl group or a trifluoromethyl group; $X^1$ is a single bond or —O—; $X^2$ and $X^3$ are independently a single bond, —CH=CH—COO—, —CH$_2$CH$_2$—COO—, —COO—, —C≡C—, or —CONH—.

5. The compound as claimed in claim 1, wherein, in formula (1), $R^1$ is a methyl or ethyl group; $R^2$ is —OCF$_3$; $A^1$ is a 1,4-phenylene group; $A^2$ and $A^3$ are independently a 1,4-phenylene group or a 3-fluoro-1,4-phenylene group; $X^1$ is a single bond or —O—; $X^2$ and $X^3$ are independently a single bond, —CH=CH—COO—, —CH$_2$CH$_2$—COO—, —COO—, —C≡C—, or —CONH—; m is an integer of from 0 to 8.

6. The compound as claimed in claim 1, wherein, in formula (1), $R^1$ is a methyl or ethyl group; $R^2$ is —OCF$_3$; $A^1$ is a 1,4-phenylene group; $A^2$ and $A^3$ are independently a 1,4-phenylene group or a 3-fluoro-1,4-phenylene group; $X^1$ is a single bond or —O—; $X^2$ and $X^3$ are independently a single bond, —CH=CH—COO—, —CH$_2$CH$_2$—COO—, —COO—, or —CONH—; m is an integer of from 0 to 6.

7. The compound as claimed in claim 1, wherein, in formula (1), $R^1$ is a methyl or ethyl group; $R^2$ is —OCF$_3$; $A^1$ is a 1,4-phenylene group $A^2$ a 1,4-phenylene group or a 3-fluoro-1,4-phenylene group; $X^1$ is a single bond or —O—; $X^2$ is —CH=CH—COO—, —CH$_2$CH$_2$—COO—, —COO—, or —CONH—; m is an integer of from 0 to 6; and n is 0.

8. The compound as claimed in claim 1, wherein, in formula (1), $R^1$ is a methyl or ethyl group; $R^2$ is —OCF$_3$; $A^1$ is a 1,4-phenylene group; $A^2$ is a 1,4-phenylene group or a 3-fluoro-1,4-phenylene group; $X^1$ is a single bond or —O—; $X^2$ is —COO—; m is an integer of from 0 to 6; and n is 0.

9. The compound as claimed in claim 1, wherein, in formula (1), $R^1$ is a methyl or ethyl group; $R^2$ is —OCF$_3$; $A^1$ is a 1,4-phenylene group; $A^2$ a 1,4-phenylene group or a 3-fluoro-1,4-phenylene group; $A^3$ is a 1,4-phenylene group; $X^1$ is a single bond or —O—; $X^2$ is —CH=CH—COO—, —CH$_2$CH$_2$—COO—, —COO—, or —CONH—; $X^3$ is a single bond; m is an integer of from 0 to 6; and n is 1.

10. The compound as claimed in claim 1, wherein, in formula (1), $R^1$ is a methyl or ethyl group; $R^2$ is —OCF$_3$; $A^1$, $A^2$ and $A^3$ is a 1,4-phenylene group; $X^1$ is a single bond or —O—; $X^2$ is —COO—; $X^3$ is a single bond; m is an integer of from 0 to 6; and n is 1.

11. A liquid-crystal composition containing at least two compounds, in which at least one compound is the compound of claim 1.

12. The liquid-crystal composition as claimed in claim 11, wherein all the compounds are polymerizable compounds.

13. The liquid-crystal composition as claimed in claim 11, wherein at least one compound is the compound of formula (1) and at least one other compound is a polymerizable compound that differs from the compound of claim 1.

14. The liquid-crystal composition as claimed in claim 11, wherein all the compounds are the compounds of formula (1).

15. The liquid-crystal composition as claimed in claim 11, which contains at least one compound of formula (1) and at least one polymerizable compound selected from a group of compounds of formulae (M1), (M2), (M3), (M4) and (M5):

atom or a cyano group; $B^1$ independently represents a single bond, a 1,4-phenylene group, a naphthalene-2,6-diyl group, a biphenyl-4,4'-diyl group, a fluorene-2,7-diyl group, a 9-methylfluoren-2,7-diyl group, a 9-ethylfluorene-2,7-diyl group, a 9,9-dimethylfluoren-2,7-diyl group, a 9-chlorofluorene-2,7-diyl group, a 9,9-difluorofluoren-2,7-diyl group, or a 1,4-phenylene group in which any hydrogen is substituted with a halogen atom, a cyano group, a methyl group or trifluoromethyl group; $Z^1$ and $Z^2$ each independently represent a single bond, —COO—, —OCO—, —CH$_2$CH$_2$—, or —C≡C—; $X^5$ and $X^6$ each independently represent a single bond or —O—; q independently indicates 1 or 0; o, p and r each independently indicate an integer of from 0 to 20.

16. The liquid-crystal composition as claimed in claim 15, which contains at least one compound of formula (1) and at least one polymerizable compound selected from the group of compounds of formula (M1) and (M2).

17. The liquid-crystal composition as claimed in claim 15, which contains at least one compound of formula (1) and at least one polymerizable compound selected from the group of compounds of formula (M3).

18. liquid-crystal composition as claimed in claim 15, which contains at least one compound of formula (1) and at least one polymerizable compound selected from the group of compounds of formulae (M4) and (M5).

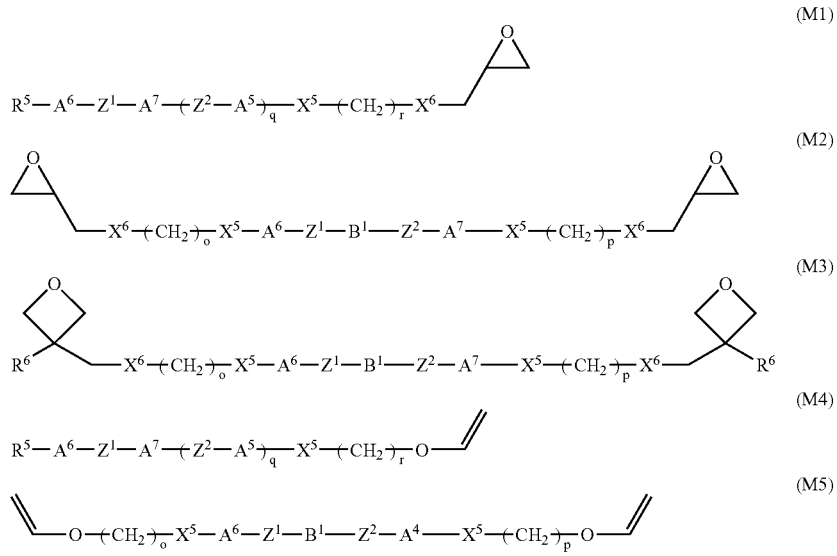

wherein $R^5$ independently represents a hydrogen atom, a fluorine atom, a chlorine atom, —CN, or an alkyl group having from 1 to 20 carbon atoms; in the alkyl group, any —CH$_2$— may be substituted with —O—, —S—, —COO—, —OCO— or —CO—, and any hydrogen may be substituted with a halogen atom; $R^6$ independently represents a hydrogen atom or an alkyl group having from 1 to 5 carbon atoms; $A^4$, $A^5$, $A^6$ and $A^7$ each independently represent a 1,4-cyclohexylene group, a 1,4-phenylene group, a pyridine-2,5-diyl group, a pyrimidine-2,5-diyl group, a naphthalene-2,6-diyl group, a fluorene-2,7-diyl group, or a 1,4-phenylene group in which any hydrogen atom is substituted with a halogen 19. The liquid-crystal composition as claimed in claim 15, which contains at least one compound of formula (1) and at least one polymerizable compound selected from the group of compounds of formula (M1), (M2) and (M3).

20. A polymer obtained by polymerizing the compound of claim 1.

21. A polymer obtained by polymerizing the composition of claim 11.

22. An optically-anisotropic shaped article comprising the polymer of claim 20.

23. A liquid-crystal display device comprising the optically-anisotropic shaped article of claim 22.

* * * * *